(12) United States Patent
Pierce et al.

(10) Patent No.: US 7,943,549 B2
(45) Date of Patent: May 17, 2011

(54) BIOLOGICAL-BASED CATALYST TO DELAY PLANT DEVELOPMENT PROCESSES

(75) Inventors: George E. Pierce, Canton, GA (US); Sangeeta Ganguly, Buffalo Grove, IL (US); Gene K. Drago, Gainesville, FL (US)

(73) Assignee: Georgia State University Research Foundation, Inc., Atlanta, GA (US)

( * ) Notice: Subject to any disclaimer, the term of this patent is extended or adjusted under 35 U.S.C. 154(b) by 713 days.

(21) Appl. No.: 11/695,377

(22) Filed: Apr. 2, 2007

(65) Prior Publication Data

US 2008/0236038 A1 Oct. 2, 2008

(51) Int. Cl.
*A01N 63/00* (2006.01)
*C12N 1/20* (2006.01)

(52) U.S. Cl. ............... 504/117; 435/252.3; 47/58.1 FV; 47/58.1 R; 47/1.01 R

(58) Field of Classification Search .................. None
See application file for complete search history.

(56) References Cited

U.S. PATENT DOCUMENTS

| | | | |
|---|---|---|---|
| 3,940,316 A | 2/1976 | Commeyras et al. | |
| 4,001,081 A | 1/1977 | Commeyras et al. | |
| 4,343,900 A | 8/1982 | Watanabe | |
| 5,512,466 A | 4/1996 | Klee et al. | |
| 5,545,815 A * | 8/1996 | Fischer et al. | 800/286 |
| 5,664,368 A | 9/1997 | Sandor | |
| 5,807,730 A | 9/1998 | Ito et al. | |
| 5,863,750 A | 1/1999 | Pierce | |
| 6,060,265 A | 5/2000 | Pierce | |
| 6,132,985 A | 10/2000 | Pierce | |
| 6,156,956 A | 12/2000 | Theologis et al. | |
| 6,194,193 B1 | 2/2001 | Drahos et al. | |
| 6,426,105 B1 | 7/2002 | Palta et al. | |
| 6,524,998 B1 | 2/2003 | Kloepper et al. | |
| 6,606,822 B2 | 8/2003 | Bonfiglio | |
| 6,649,397 B1 | 11/2003 | Nakamura | |
| 6,735,902 B1 | 5/2004 | Ahm | |
| 6,955,911 B2 | 10/2005 | Ryuno et al. | |
| 7,084,321 B2 | 8/2006 | Pais et al. | |
| 7,213,366 B1 | 5/2007 | Ahm | |
| 7,244,595 B2 | 7/2007 | Uehara et al. | |
| 7,504,557 B2 * | 3/2009 | Gallie et al. | 800/283 |
| 7,531,343 B2 | 5/2009 | Pierce et al. | |
| 7,531,344 B2 | 5/2009 | Pierce et al. | |
| 2002/0139046 A1 | 10/2002 | Weber et al. | |
| 2003/0044807 A1* | 3/2003 | Bramucci et al. | 435/6 |
| 2003/0084609 A1 | 5/2003 | Perriello et al. | |
| 2003/0093946 A1 | 5/2003 | Gutierrez Pavez | |
| 2003/0115633 A1 | 6/2003 | Pais et al. | |
| 2004/0072694 A1 | 4/2004 | Jacobson et al. | |
| 2005/0000154 A1 | 1/2005 | Perriello et al. | |
| 2005/0014243 A1 | 1/2005 | Uehara et al. | |
| 2005/0227356 A1* | 10/2005 | Lessard et al. | 435/476 |
| 2007/0068072 A1 | 3/2007 | Xavier et al. | |
| 2007/0184528 A1 | 8/2007 | Pierce | |
| 2007/0184543 A1 | 8/2007 | Pierce | |
| 2007/0259783 A1 | 11/2007 | Tateishi et al. | |
| 2008/0236038 A1 | 10/2008 | Pierce et al. | |

FOREIGN PATENT DOCUMENTS

| | | |
|---|---|---|
| EP | 109083 | 5/1984 |
| EP | 0243 966 | 11/1987 |
| EP | 0243 967 | 11/1987 |
| EP | 0307926 | 3/1989 |
| JP | 54129190 | 10/1979 |
| JP | 2000470 | 1/1990 |
| JP | 5030983 | 2/1993 |
| JP | 5236977 | 9/1993 |
| JP | 8056684 | 3/1996 |
| JP | 8154691 | 6/1996 |
| JP | 8187092 | 7/1996 |
| WO | WO 92/12249 | 7/1992 |
| WO | WO 00/36085 | 6/2000 |
| WO | WO 00/51435 | 9/2000 |
| WO | WO 03/037066 | 5/2003 |
| WO | WO 03/041491 | 5/2003 |
| WO | WO 2008/124307 | 10/2008 |

OTHER PUBLICATIONS

Kozdroj et al., "Influence of introduced potential biocontrol agents on maize seedling growth and bacterial community structure in the rhizosphere" *Soil Biology and Biochemistry* 36(11):1775-1784 (2004).
Kulikova et al., "Ethylene epoxidation by native and immobilized cells of the propane-assimilating culture *Rhodococcus erythropolis* 3/89" *Prikladnaya Biokhmiya I Mikrobiologiya* 35(6):611-615 (1999).
Reed et al., "Delayed ripening tomato plants expressing the enzyme 1-aminocyclopropane-1-carboxylic acid deaminase. 1. Molecular characterization, enzyme expression, and fruit ripening traits" *Journal of Agriculture and Food* 43:1954-1962 (1995).
Wang, Z., et al., 2003, "An in vivo experimental system to study sugar phloem unloading in ripening grape berries during water deficiency stress," Annals of Botany, 92: 523-528.
Wang, K.L.C., et al., 2002, "Ethylene biosynthesis and signaling networks," The Plant Cell, Supplement 2002, S131-S151. Wang et al., 2004. "Regulation of ethylene gas biosynthesis by the *Arabidopsis* ETI protein." Nature. 428: 945-950.
Watanabe et al. "Screening, Isolation And Taxonomical Properties of Microorganisms Having Acrylonitrile Hydrating Activity", *Agric. Biol. Chem.*, 1987, pp. 3193-3199, vol. 51.
Watkins, C.B., and C. Frenkel, 1987, "Inhibition of pear fruit ripening by mannose," Plant Physiol., 85: 56-61.
Weingart, H. and B. Volksch. 1997. "Ethylene production by *Pseudomonas syringae* pathovars in vitro and in planta." Appl. Environ. Microbiol. 63 : 156-161.
Whittaker, D. J., G. S. Smith, and R. C. Gardner. 1997. "Expression of ethylene biosynthetic genes in *Actinidia chinensis* fruit" Plant Molec. Biol. 343: 45-55.

(Continued)

*Primary Examiner* — Lisa J Hobbs

(74) *Attorney, Agent, or Firm* — McKeon Muenier Carlin Curfman

(57) ABSTRACT

The present invention is directed to methods for delaying a plant development process comprising exposing a plant or plant part to one or more bacteria or enzymes. In specific embodiments, the one or more bacteria are selected from the group consisting of *Rhodococcus* spp., *Pseudomonas chloroaphis, Brevibacterium ketoglutamicum*, and a mixture comprising any combination of these bacteria. Apparatuses for delaying a plant development process comprising a catalyst that comprises one or more of the above bacteria.

51 Claims, 3 Drawing Sheets

OTHER PUBLICATIONS

Wild, I.Y., 1998, "Controlled atmosphere update: a cost benefit analysis—horses for courses," Intermodal 1998 Conference, Dec. 1-3, 1998, Rotterdam, www.drwild.de/1998-12-02_Intermodal_CA.pdf.

Woolf et al., 2005. "I -MCP reduces physiological storage disorders of "Hass" avocados." Postharvest Biol. Technol. 35: 43-60.

Woltering, E. J. 1990. "Interorgan translocation of 1 - aminocyclopropane-1 -carboxylic acid and ethylene coordinates senescence in emasculated Cymbidium flowers." Plant Physiol. 92:837-845.

Woodson et al., 1992. "Expression of ethylene biosynthetic pathway transcripts in senescing carnation flowers." Plant Physiol. 99: 526-532.

Woodson, W.R., and K.A. Lawton, 1988 "Ethylene-induced gene expression in carnation petals," Plant Physiol., 87: 498-503.

Yamada, et al., "Optimum culture conditions for production by Pseudomonas chloroaphis B23 of nitrile hydratase" Agric. Biol. Chem. 1986, pp. 2859-2865, vol. 50, No. 11.

Yang, S. F. And N. E. Hoffman. 1984. "Ethylene biosynthesis and its regulationin higher plants." Ann. Rev. Plant Physiol. 35: 155-1 89.

Zhao, J., et al., 2005, "Elicitor signal transduction leading to production of plant secondary metabolites," Biotechnology Advances, 23 : 283-333.

Beaudoin et al., "Interactions between abscisic acid and ethylene signaling cascades," The Plant Cell 12:1103-15 (2000).

Bleecker and Kende, "Ethylene: a gaseous signal molecule in plants," Annu. Rev. Cell Dev. Biol. 16:1-18 (see abstract) (2000).

Nagasawa et al., "Characterization of a new cobalt-containing nitrile hydratase purified from urea-induced cells of Rhodococcus rhodochrous J1," Eur. J. Biochem. 196:581-589 (1991).

Alexander and Grierson, "Ethylene biosynthesis and action in tomato: a model for climacteric fruit ripening" J. Exp. Botany, 53:2039-2055 (2002).

Avni et al., "Induction of ethylene biosynthesis in Nicotiana tabacum by a Trichoderma viride sylanase is correlated to the accumulation of 1-aminocyclopropane-l-carboxylic acid (ACC) synthase and ACC oxidase transcripts" Plant Physiol. 106:1049-1055 (1994).

Badr et al., "Kinetics and properties of L-glutaminase and L-asparaginase activities of Pseudomonas ovalis," Badt. II. Abt. 1976, pp. 489-496, vol. 131.

Bahr, J. T. and W. D. Bonner, Jr. 1973. "Cyanide-insensitive respiration" J. Biol. Chem. 248: 3446-3450.

Bates, B.R., and H. Warner, Nov. 2001, "1-MCP and Fruit Quality," Perishables Handling Quarterly, Issue No. 108, postharvest.ucdavis.edu/datastorefiles/234-37.pdf.

Bijnen et al., 1996. "Geometrical optimization of a longitudinal resonant photoacoustic cell for sensitive and fast trace gas detection." Rev. Sci. Instrum. 67: 29 14-2923.

Blankenship, S. M. and J. M. Dole. 2003. "1-Methylcyclopropene: a review." Postharvest Biol. Technol. 28: 1-25.

Bleecker, A. B. and H. Kende. 2000. "Ethylene: a gaseous signal molecule in plants." Ann. Rev. Cell. Dev. Biol. 16: 1-18.

Bowyer, M.C., and R.B.H. Wills, May 2003, "Delaying postharvest senescence of cut flowers using nitric oxide," Rural Industries Research and Development Corporation, www.rirdc.gov.au/reports/WNP/03-015.pdf.

Bunch et al., "Biotransformation of nitriles by Rhodococci" Antonie van Leeuwenhoek, 1998, pp. 89-97, vol. 74, Kluwer Academic Publishers, The Netherlands.

Caron, Environmental Test Chambers, http://www.caronproducts.com/18/prodcat/all, Jun. 2005.

Chamani, E., et al., 2005, "Ethylene and anti-ethylene treatment effects on cut 'First Red' rose," Journal of Applied Horticulture, 7(1):3-7.

"Chiquita explores financial alternatives," Refrigerated Transporter, Sep. 29, 2006, http://refrigeratedtrans.com/marr/transpoation_chiquita_explores_financial/index.html.

Cincinnati Sub-zero, Microclimate Benchtop Test Chambers, http://www.cszindustrial.com/products/microclimate/microclimate, 2006.

Crassweller, R., 2000, Pennsylvania State University, Horticulture 432, Lecture Notes: Thinning and PGRs, www.hortweb.cas.psu.edu/courses/hort432/lecturenotes/pgr.html.

Crisoto, C., 1994, "Stone fruit maturity indices: a descriptive review," Postharvest News and Information, vol. 5 No. 6, 65N-68N.

Cristescu et al., 2002. "Ethylene production by Botrytis cinerea in vitro and in tomatoes." Appl. Environ. Microbial. 68: 5342-5350.

Curry, E., and J. Thompson, 1999, "Delicious quality can be affected by ethephon or ReTain," Washington University—Tree Fruit Research and Extension Center: Postharvest Information Network, 1 5th Annual Postharvest Conference, Mar. 9-10, 1999, http://postharvest.tfrec.wsu.edu/pgDisplay.php?article=PC99A.

Dixon, R. A. and N. L. Palva. 1995. "Stress-induced phenylpropanoid metabolism." Plant Cell. 7: 1085-1097.

Dole Worldwide: Latin America and Caribbean, http://www.dole.com/CompanyInfo/About/Worldwide/LatinAmerica.isp, printed Oct. 18, 2006.

Dominguez et al., 1998. "Effect of inhibitors of ethylene biosynthesis and action on ripening of bananas." Proc. Int. Symp. Bananas in Subtropics (V. Galan Sauco, Editor) 519-528.

Dong, J., et al., 1992, "Purification and characterization of 1 -aminocyclopropane-1-carboxylate oxidase from apple fruit," Proc. Natl. Acad. Sci. USA, 89: 9789-9793.

El-Sharkawy et al., 2003. "Isolation and characterization of four ethylene perception elements and their expression during ripening in perars (Pyrus communis L.) with/without cold requirement." J Exp. Botany. 54: 161 5-1 625.

Fawcett et al., "A Rapid and Precise Method for the Determination of Urea", J. Clin. Path., 1960, pp. 156-159, vol. 13.

Foda et al., "Formation and properties of L-glutaminase and L-asparaginase activities in Pichia polymorpha," Acta Microbiol. Pol. 1980, pp. 343-352, vol. 29, No. 4.

Fisher et al., "Bacillus subtilis 168 contains two differentially regulated genes encoding L-asparaginase" J. Bacteriol. 2002, pp. 2148-2154, Vo. 184, No. 8.

Floratech, Tips on Keeping Flowers Healthy, http://www.floratech.net/New/%C2%BFmode=view_page&page_id=20.html, Dec. 19, 2002.

Fruit Control Equipment, Product Technical Catalog, CA Pilot Cabinets, http://www.fruitcontrol.it/prodottinglese/cabinet.htm.

Fournand et al., "Acyl tranfer activity of an amidase from Rhodococcus sp. Strain R312: Formation of a wide range of hydroxamic acids" Applied and Environmental Microbiology 1998, pp. 2844-2852, vol. 64, No. 8.

Gas Control Systems, Ethylene Analyser GCS-560, www.gascontrolsystems.com, 2003.

GEO-PIE Project: Delayed fruit ripening, www.geopie.cornell.edu~traits/fruitrip.html, Printed Sep. 25, 2006.

Goda et al., "Discovery of a novel enzyme, isonitrile hydratase, involved in nitrogen-carbon triple bond cleavage" J. Biol. Chem. 276(26):23480-23485 (2001).

Hann et al., "5-Cyanovaleramide Production Using Immobilized Pseudomonas chlororaphis B23", Bioorg. Medicinal Chem., 1999, pp. 2239-2245, vol. 7.

Huber, et al., 2003, "Use of 1-methylcyclopropene (1-MCP) on tomato and avocado fruits: potential for enhanced shelf life and quality retention," University of Florida, IFAS Extension, http://edis.ifas.ufl.edu/HS151.

International Labour Organization, "The world cut flower industry: trends and prospects," http://www.ilo.org/public/englishldialoue/sector/papers/ctflower/139e2.htm, 2000.

Itai et al., 2003. "Rapid identification of 1 -minocyclopropane- 1 - carboxylate (ACC) synthase genotypes in cultivars of Japanese pear (Pyruspyrifolia nakai) using CAPS markers." Theor. Appl. Genet. 106: 1266-1272.

Johnson, P. R. and J. R. Ecker. 1998. "The ethylene gas signal transduction pathway: a molecular perspective." Ann. Rev. Genetics. 32: 227-254.

Kader, A.A., 2001, "A summary of CA requirements and recommendations for fruits other than apples and pears," Postharvest Horticulture Series No. 22A, University of California, Davis, pp. 29-70.

Kader, et al., "Postharvest handling and physiology of horticultural crops: a list of selected references," University of California Postharvest Group. May 2001.

Kato, et al., "Nitrile hydratase involved in aldoxime metabolism from *Rhodococcus* sp. strain YH3-3 purification and characterization" *Eur. J. Biochem.* 263(3):662-70 (1999).

Klee et al., 1991. "Control of ethylene synthesis by expression of a bacterial enzyme in transgenic tomato plants." Plant Cell. 3: 1 187-1 193.

Komeda, et al., Characterization of the gene cluster of high-molecular-mass nitrile hydratase (H-NHase) induced by its reaction produce in *Rhodococcus rhodochrous* J1: *PNAS*, 1996, vol. 93, pp. 4267-4272.

Kopf et al., "Key Role Of Alkanoic Acids On The Spectral Properties, Activity, and Active-Site Stability of Iron-Containing Nitrile Hydratase From Brevibacterium R312", Eur J. Biochem., 1996, pp. 239-244, vol. 240.

Lafuente et al., 2001. "Phenylalanine ammonia-lyase as related to ethylene in the development of chilling symptoms during cold storage of citrus fruit." J. Agric. Food Chem. 49: 6020-6025.

Lawton, K.A., et al., 1990, "Regulation of senescence-related gene expression in carnation flower petals by ethylene," Plant Physiol., 93: 1370-1 375.

Liao, L., et al., 2000, "Postharvest life of cut rose flowers as affected by silver thiosulfate and sucrose," Bot. Bull. Acad. Sin., 41: 299-303.

Mafra, I., et al., 2006, "Ripening-related changes in the cell walls of olive (*Olea europea* L.) pulp of two consecutive harvests, J. Sci. Food Agric. 86: 988-998.

Marcos et al., 2005. "Involvement of ethylene biosynthesis and perception in the susceptibility of citrus fmits to *Penicillium digitatum* infection and the accumulation of defence-related mRNAs." J. Exp. Botany. 56: 21 83-2193.

Martinkova, et al., "Nitrile- and amide-converting microbial enzymes: stereo-, regio-chemoselecivity" *Biocatalysis and Biotransformation*, 2002, pp. 73-93, vol. 20, No. 2.

Mathooko, F. M., 1996, "Regulation of ethylene biosynthesis in higher plants by carbon dioxide," Postharvest Biology and Technology, 7: 1-26.

Mayak, S., and D.R. Dilley, 1976, "Regulation of senescence in carnation (*Dianthus caryophyllus*): effect of absiscic acid and carbon dioxide on ethylene production," Plant Physiol., 58: 663-665.

Mayak, S., and A.H. Halevy, 1972, "Interrelationships of ethylene and abscisic acid in the control of rose petal senescence," Plant Physiol., 50: 341-346.

McDaniel, A., 1999, Virginia Polytechnic University, Horticulture 2164 Lecture Notes, R-8, http://www.hort.vt.edu/faculty/McDaniel/hort2164/R&DistributionandHandling.htm.

Merritt et al., 2001. "Inhibitors of ethylene synthesis inhibit auxin-induce stomatal opening in epidermis detached from leaves of *Vicia faba* L." Plant Cell Physiol42: 223-230.

Mullins, T., 2000, University of Florida, BOT 6566 (Plant Growth and Development), Lecture Notes 12: Seed and Fruit Development.

Nagasawa et al., "Optimum Culture Conditions for the Production of Benzonitrilase by *Rhodococcus rhodochrous*" J1. Arch. Microbiol., 1988, pp. 89-94, vol. 150.

Nagasawa et al., "Occurrence of a Cobalt-Induced and Cobalt-Containing Nitrile Hydratase in *Rhodococcus rhodochrous*", J1. Biochem. Biophys. Res. Comm., 1988, pp. 1008-1016, vol. 155.

Nagasawa, et al., "Optimum culture conditions for the production of cobalt-containing nitrile hydratase by *Rhodococcus rhodochrous* J1" *Applied Microbiology and Biotechnology* 1991, pp. 783-8, vol. 34.

Nagasawa et al., "Nitrilase of *Rhodococcus rhodochrous* J1. Conversion into the active form by subunit association" *Eur. J. Biochem.* 267(1):138-44 (2000).

Nukui, H., et al., 2004, "Repressed ethylene production in the gynoecium of longlasting flowers of the carnation 'White Candle': role of the gynoecium in carnation flower senescence," Journal of Experimental Botany, 55 (397): 641-650.

Pandey S. et al., 2000, "Role of polyamines and ethylene as modulators of plant senescence," J. Biosci., 25(3): 291-299.

Pesis, et al., Project Abstract, Postharvest delay of fruit ripening by metabolites of anaerobic respiration: acetaldehyde and ethanol. http://www.bard-isus.com/FRAbst/1787.htm, printed Sep. 25, 2006.

Pesis, E., and D. Faiman, 1995, "Inhibition of ethylene production and ACC oxidase activity in avocado by acetaldehyde vapours," Proceedings of the World Avocado Congress 111,354-361, www.avocadosource.com/WAC3/WAC3 p354.htm.

Plant-Hormones, Ethylene, http://www.plant-hormones.info/ethylene.htm, printed Sep. 25, 2006.

Pretel et al., 1999. Ripening and ethylene biosynthesis in controlled atmosphere stored apricots. Eur. Food Res. Technol. 209: 130-134.

Pujade-Renaud et al., 1994. "Ehtylene-induced increase in glutamine synthetase activity and mRNA levels in *Hevea brasiliensis* latex cells." Plant Physiol. 100: 13 1-127.

Radboud University, Plant hormone ethylene and detection, http://www.ru.nl/tracenasfacility/life_science_trace/plant_physiology/plant_hormone/.

Rhodes, D., 2008, Purdue University, Horticulture 640—Metabolic Plant Physiology, http://www.hort.purdue.edu/rhodcv/hort640c/sulfate/su00009.htm.

Rychter et al., 1978. "Cyanide-resistant respiration in freshly cut potato slices." Plant Physiol. 61: 667-668.

Sacher, J.A., 1966, "Permeability characteristics and amino acid incorporation during senescence (ripening) of banana tissue," Plant Physiol., 4 1 : 701-708.

Saltveit, M. E. 2006. University of California, Davis. Department of Vegetable Crops. Postharvest Technology Research Information Center [PTRIC] "Respiratory Metabolism". postharvest.ucdavis.edu.

Sankhian, et al., "Nitrile hydratase of *Rhodococcus rhodochrous* NHB-2: optimization of conditions for production of enzyme and conversion of acrylonitrile to acrylamide" *Asian Jr. of Microbiol. Biotech.*, 2003, pp. 217-233, vol. 5, No. 2.

Singh et al., 1994. "Effect of cobalt, cadmium, and nickel as inhibitors of ethylene biosynthesis on floral malformation, yield, and fruit quality of mango" J. Plant Nutrition. 17: 1659-1670.

Sisler et al., 1999. "Inhibition of ethylene responses by 1 -methylcyclopropene and 3-methylcycloproene." Plant Growth Reg. 27: 105-111.

SLX International, Inc. 2002. User manual and instructions for the SLX International, Inc. model 2024 shipping container. SLX International, Inc. San Luis Obispo, CA.

Solomos, T. and G. G. Laties. 1974. "Similarities between the actions of ethylene and cyanide in initiating the climacteric ripening of avocados." Plant Physiol. 54: 506-511.

Sonawane, et al., "Utilization of acidic amino acids and their amides by *Pseudomanads*: role of periplasmic glutaminase-asparaginase" *Arch. Microbiol.* 2003, pp. 151-159, vol. 179.

Sonawane, et al., "Identification of *Pseudomonas* proteins coordinately induced by acidic amino acids and their amides: a two-dimensional electrophoresis study" *Microbiology*, 2003, pp. 2909-2918, vol. 149.

Soong, et al., "A novel amidase (half-amidase) for half-amide hydrolysis involved in the bacterial metabolism of cyclic imides" *Appl. Environ. Microbiol.* 66(5):1947-52 (2000).

Sozzi, G.O., et al., 2002, "Gibberellic acid, synthetic auxins, and ethylene differentially modulate a-I,-arabinofwanosidase activities in antisense 1 -aminocyclopropane- 1 -carboxylic acid synthase tomato pericarp discs," Plant Physiol., 129: 1330-1340.

ten Have, A. and E. J. Woltering. 1997. "Ethylene biosynthetic genes are differentially expressed during carnation (*Dianthus caryophyllus* L.) flower senescence" Plant Molec. Biol. 34: 89-97.

Thompson, J.E., et al., 1982, "Acceleration of membrane senescence in cut carnation flowers by treatment with ethylene," Plant Physiol., 69: 859-863.

Trainotti, L. A. Pavanello, and G. Casadoro. 2005. Different ethylene receptors show an increased expdression during the ripening of strawberries: does such an increment imply a role for ethylene in the ripening of these non-climateric fruits. J. Exp. Botany. 56: 2037-2046.

Tudela, D. and E. Primo-Millo. 1992. "I -Aminocyclopropane- 1 -carboxylic acid transported from roots to shoots promotes leaf abscission in Cleopatra Mandarin (*Citrus reshni* Hort. ex Tan.) seedlings rehydrated after water stress." Plant Physiology 100:131-137.

USDA, Agricultural Export Transportation Handbook: Maintaining Product Quality During Transportation, http://www.rockymountainbusiness.com/AgExporters/maintaining_product_quality.htm, printed Oct. 23, 2006.

USDA. 2006. Tropical Products Transport Handbook. USDA [usda.gov/tmd/Tropical].

U.S. Global Resources, Plant Growth 1 Germination Cabinets, www.usgr.com.

Van Doorn "Does Ethylene Treatment Mimic the Effects of Pollination on Floral Lifespan and Attractiveness?" Annals of Botany 89:375-383 (2002).

Van Doorn, "Effect of Ethylene on Flower Abscission: a Survey" Annals of Botany 89:689-693 (2002).

Van Doorn, "Categories of petal senescence and abscission: a re-evaluation" Annals of Botany 87:447-56 (2001).

Wagstaff et al., 2005. "Ethylene and flower longevity in *Alstroemeria*: relationship between tepal senescence, abscission and ethylene biosynthesis." J. Exp. Botany. 56:1007-1016.

* cited by examiner

BIOLOGICAL-BASED CATALYST TO DELAY PLANT DEVELOPMENT PROCESSES

FIELD OF THE INVENTION

The present invention relates to methods for delaying a plant development comprising exposing a plant or plant part to one or more bacteria or enzymes. Apparatuses for delaying a plant development process are further provided.

BACKGROUND OF THE INVENTION

Ethylene production in plants and plant parts is induced by a variety of external factors and stressors, including wounding, the application of hormones (e.g., auxin), anaerobic conditions, chilling, heat, drought, and pathogen infection. Increased ethylene production also is observed during a variety of plant development processes, including fruit or vegetable ripening, seed germination, leaf abscission, and flower senescence.

Ethylene biosynthesis in plants is typically depicted as an enzymatic scheme involving three enzymes, traditionally referred to as the "Yang Cycle," in which S-adenosyl-L-methionine (SAM) synthase catalyzes conversion of methionine to S-adenosyl-L-methionine (AdoMet); 1-aminocyclopropane-1-carboxylic acid (ACC) synthase catalyzes the conversion of AdoMet to ACC; and ACC oxidase catalyzes the conversion of ACC to ethylene and the byproducts carbon dioxide and hydrogen cyanide. See, for example, Srivastava (2001) *Plant Growth and Development: Hormones and Environment* (Academic Press, New York) for a general description of ethylene biosynthesis in plants and plant development processes regulated by ethylene.

Previous research has established that in climacteric fruit ripening is triggered, at least in part, by a sudden and significant increase in ethylene biosynthesis. Although a sudden burst of ethylene production is implicated in the fruit ripening process of climacteric fruits, the exact mechanism, particularly in nonclimacteric fruits, is not completely understood. While there is no sudden burst of ethylene production in non-climacteric fruit, non-climacteric fruit will respond to ethylene. Moreover, fruits, vegetables, and other plant products vary in the amount of ethylene synthesized and also in the sensitivity of the particular product to ethylene. For example, apples exhibit a high level of ethylene production and ethylene sensitivity, whereas artichokes display a low level of ethylene biosynthesis and ethylene sensitivity. See, for example, Cantwell (2001) "Properties and Recommended Conditions for Storage of Fresh Fruits and Vegetables" at postharvest.ucdavis.edu/Produce/Storage/index.shtml (last accessed on Mar. 6, 2007), which is herein incorporated by reference in its entirety. Fruit ripening typically results in a change in color, softening of the pericarp, and changes in the sugar content and flavor of the fruit. While ripening initially makes fruit more edible and attractive to eat, the process eventually leads to degradation and deterioration of fruit quality, making it unacceptable for consumption, leading to significant commercial monetary losses. Control of the ripening process is desirable for improving shelf-life and extending the time available for transportation, storage, and sale of fruit and other agricultural products subject to ripening.

In addition to a sudden increase in ethylene biosynthesis in climacteric fruits, ripening-related changes are also associated with a rise in respiration rate. Heat is produced as a consequence of respiration in fruit, vegetables, and other plant products and, consequently, impacts the shelf-life and the required storage conditions (e.g., refrigeration) for these commodities. Plant products with higher rates of respiration (e.g., artichokes, cut flowers, asparagus, broccoli, spinach, etc.) exhibit shorter shelf-lives than those with lower respiration rates (e.g., nuts, dates, apples, citrus fruits, grapes, etc.). Respiration is affected by a number of environmental factors including temperature, atmospheric composition, physical stress, light, chemical stress, radiation, water stress, growth regulators, and pathogen attack. In particular, temperature plays a significant role in respiration rate. For a general description of respiratory metabolism and recommended controlled atmospheric conditions for fruits, vegetables, and other plant products see, for example, Kader (2001) *Postharvest Horticulture Series* No. 22A:29-70 (University of California—Davis); Saltveit (University of California—Davis) "Respiratory Metabolism" at usna.usda.gov/hb66/019respiration.pdf (last accessed on Mar. 6, 2007); and Cantwell (2001) "Properties and Recommended Conditions for Storage of Fresh Fruits and Vegetables" at postharvest.ucdavis.edu/Produce/Storage/index.shtml (last accessed on Mar. 6, 2007), all of which are herein incorporated by reference in their entirety.

Methods and compositions for delaying the fruit ripening process include, for example, the application of silver salts (e.g., silver thiosulfate), 2,5-norbornadiene, potassium permanganate, 1-methylcyclopropene (1-MCP), cyclopropene (CP) and derivatives thereof. These compounds have significant disadvantages, such as the presence of heavy metals, foul odors, and explosive properties when compressed, that make them unacceptable for or of limited applicability for use in the food industry. Transgenic approaches for controlling ethylene production to delay plant development processes (e.g., fruit ripening) by introducing nucleic acid sequences that limit ethylene production, particularly by reducing the expression of the enzymes ACC synthase or ACC oxidase, are also under investigation. The public's response to genetically modified agricultural products, however, has not been entirely favorable.

Accordingly, a significant need remains in the art for safe methods and apparatuses to delay plant development processes. Such methods and apparatuses could provide better control of fruit ripening, vegetable ripening, flower senescence, leaf abscission, and seed germination and extend the shelf-life of various agricultural products (e.g., fruit, vegetables, and cut flowers), thereby permitting longer distance transportation of these products without the need for refrigeration, increasing product desirability to consumers, and decreasing monetary costs associated with product loss due to untimely ripening and senescence.

BRIEF SUMMARY OF THE INVENTION

Methods for delaying a plant development process, including but not limited to fruit ripening, vegetable ripening, flower senescence, and leaf abscission, are provided. The methods of the present invention generally comprise exposing a plant or plant part to one or more bacteria in a quantity sufficient to delay the plant development process of interest. In certain aspects of the invention, the bacteria are selected from the group consisting of *Rhodococcus* spp., *Pseudomonas chlororaphis, Brevibacterium ketoglutamicum*, and mixtures thereof. The bacteria used in the practice of the present methods may be further treated with an inducing agent, including for example asparagine, glutamine, cobalt, urea, and mixtures thereof, to induce the ability of the bacteria to delay a plant development process of interest.

The present invention further provides apparatuses for delaying a plant development process comprising a catalyst that comprises one or more of bacteria, particularly *Rhodococcus* spp., *Pseudomonas chloroaphis*, *Brevibacterium ketoglutamicum*, or a mixture thereof. Any apparatus that permits exposure of a plant or plant part to the catalyst and delays the plant development process of interest is encompassed by the present invention. Exemplary apparatuses include those in which the catalyst is immobilized in a matrix and placed in, placed on, or otherwise affixed to any physical structure. Various configurations of the disclosed apparatuses are envisioned and described in greater detail herein below. The methods and apparatuses of the invention for delaying a plant development process find particular use in increasing shelf-life and facilitating longer-distance transportation of plant products such as fruits, vegetables, and flowers, improving consumer product satisfaction, and reducing product loss resulting from untimely ripening or senescence.

BRIEF DESCRIPTION OF THE DRAWINGS

Figure 1:
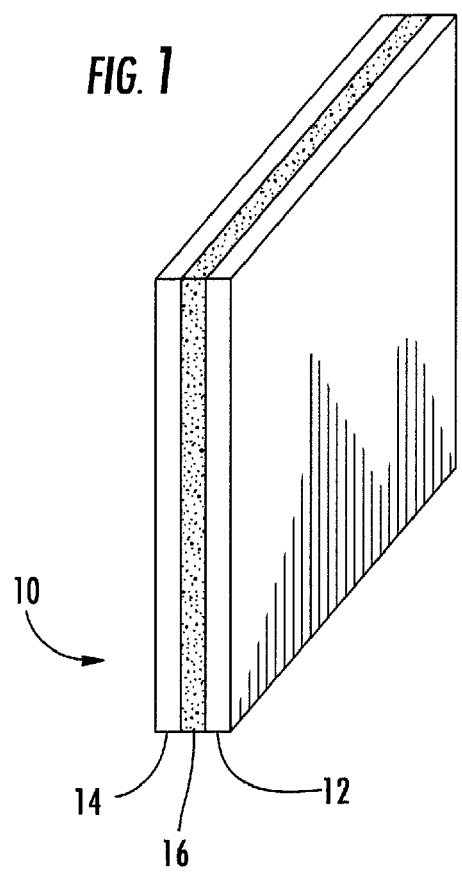

Having thus described the invention in general terms, reference will now be made to the accompanying drawings, which are not necessarily drawn to scale, and wherein:

FIG. 1 shows a non-limiting depiction of a three-layer apparatus for retarding fruit ripening. The outer layers (designated A and B) provide structural integrity to the apparatus. The catalyst layer, as defined herein below, comprises one or more of the enzymes of the invention and is located between the outer layers.

Figure 2A:
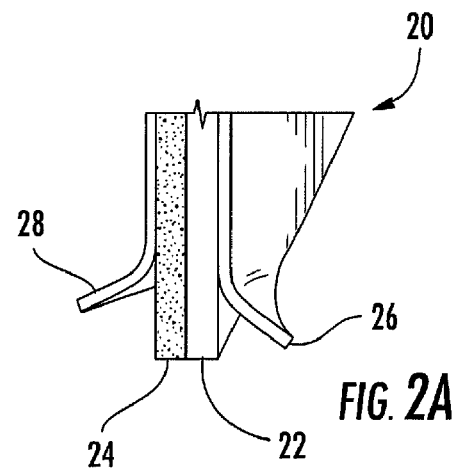
Figure 2B:
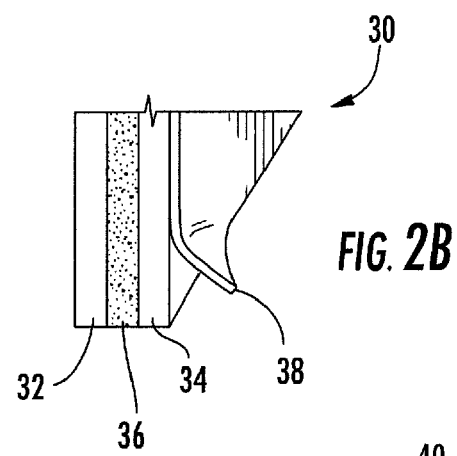
Figure 2C:
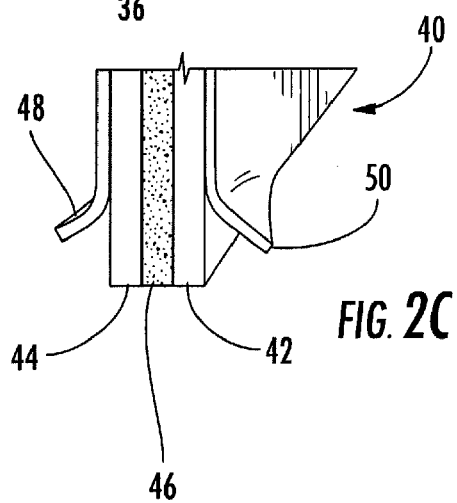

FIG. 2A-C provides non-limiting depictions of various apparatuses for retarding fruit ripening. These apparatuses comprise a catalyst layer, one or more layers intended to provide structural integrity, and one or more layers intended to be removed prior to use of the apparatus. Removal of one or more of these layers may, for example, expose an adhesive for attachment of the apparatus to another physical structure.

Figure 3A:
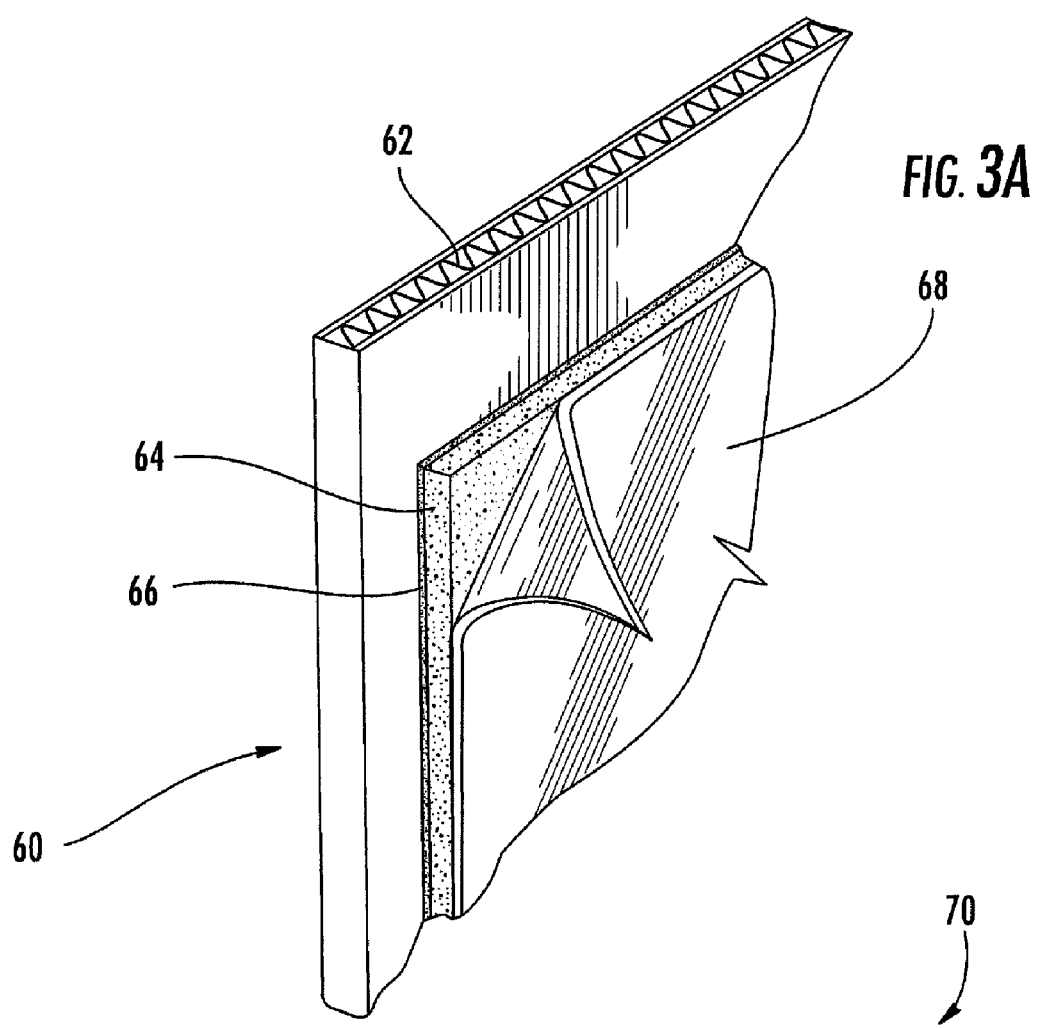
Figure 3B:
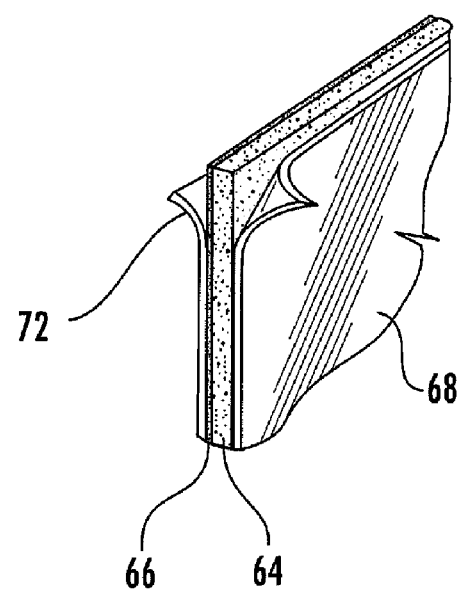

FIGS. 3A-3B show a non-limiting depiction of an apparatus for retarding fruit ripening. The apparatus comprises a catalyst immobilized on a layer of film and attached to a physical structure (e.g., a box suitable for storage/transportation of fruit).

Figure 4:
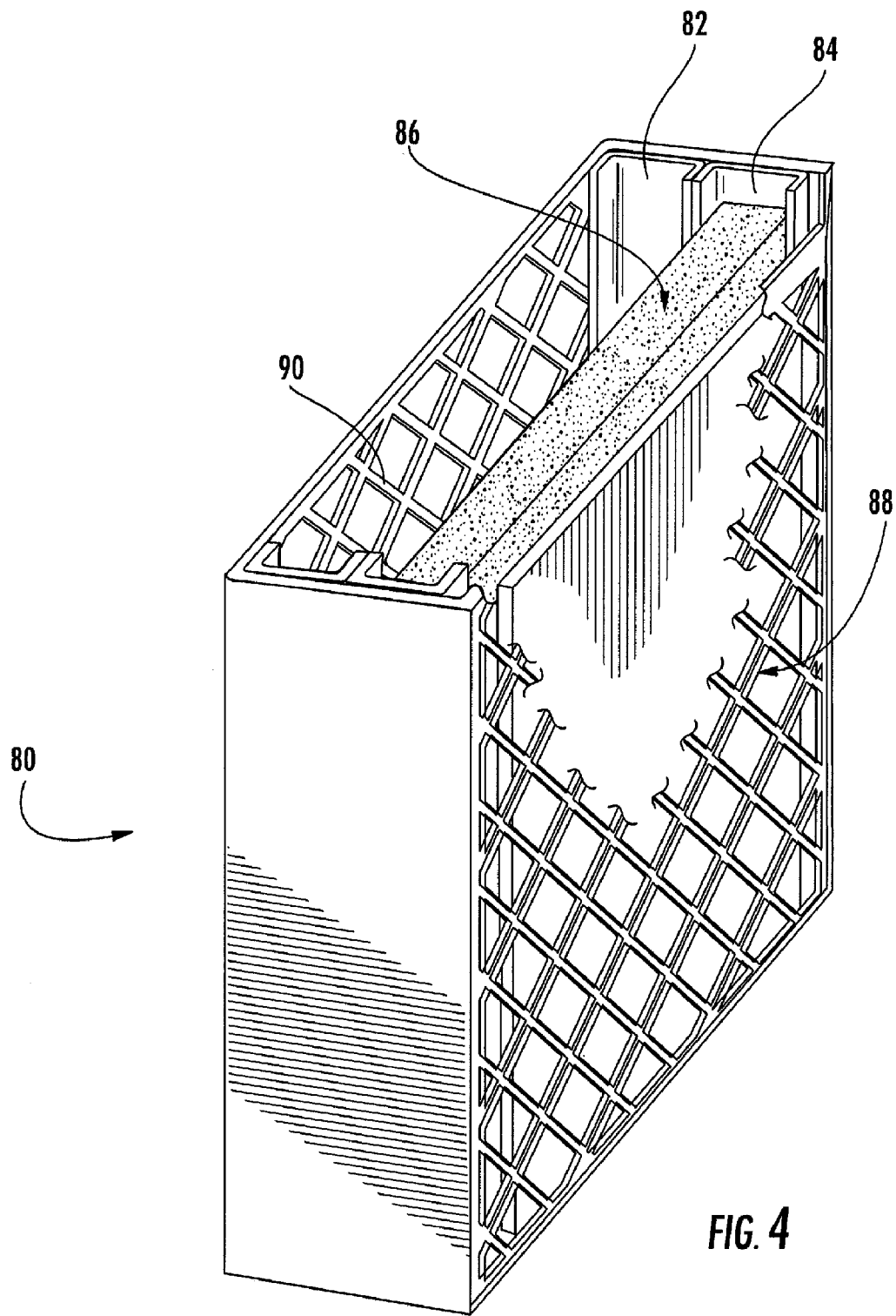

FIG. 4 provides a non-limiting depiction of an apparatus for retarding fruit ripening. The apparatus comprises a slotted chamber structure that permits the insertion and replacement of one or more catalyst module elements, as defined below. The outer layers of the physical structure may be composed of a material that permits air to flow into the catalyst.

DETAILED DESCRIPTION OF THE INVENTION

The present inventions now will be described more fully hereinafter with reference to specific embodiments of the invention and particularly to the various drawings provided herewith. Indeed, the invention may be embodied in many different forms and should not be construed as limited to the embodiments set forth herein; rather, these embodiments are provided so that this disclosure will satisfy applicable legal requirements. As used in the specification, and in the appended claims, the singular forms "a", "an", "the", include plural referents unless the context clearly dictates otherwise.

Throughout the specification the word "comprising," or grammatical variations thereof, will be understood to imply the inclusion of a stated element, integer or step, or group of elements, integers or steps, but not the exclusion of any other element, integer or step, or group of elements, integers or steps.

The present invention provides methods for delaying a plant development process of interest comprising exposing a plant or plant part to one or more bacteria. In particular embodiments, the methods are drawn to delaying a plant development process comprising exposing a plant or plant part to one or more bacteria selected from the group consisting of *Rhodococcus* spp., *Pseudomonas chloroaphis*, *Brevibacterium ketoglutamicum*, and mixtures thereof, wherein the one or more bacteria are exposed to the plant or plant part in a quantity sufficient to delay the plant development process. Apparatuses for delaying a plant development process of interest and for practicing the methods described herein are further provided. The inventive methods and apparatuses of the invention may be used, for example, to delay fruit/vegetable ripening or flower senescence and to increase the shelf-life of fruit, vegetables, or flowers, thereby facilitating transportation, distribution, and marketing of such plant products.

As used herein, "plant" or "plant part" is broadly defined to include intact plants and any part of a plant, including but not limited to fruit, vegetables, flowers, seeds, leaves, nuts, embryos, pollen, ovules, branches, kernels, ears, cobs, husks, stalks, roots, root tips, anthers, and the like. In particular embodiments, the plant part is a fruit, vegetable, or flower. In certain aspects of the invention, the plant part is a fruit, more particularly a climacteric fruit, as described in more detail below.

The methods and apparatuses of the invention are directed to delaying a plant development process, such as a plant development process generally associated with increased ethylene biosynthesis. "Plant development process" is intended to mean any growth or development process of a plant or plant part, including but not limited to fruit ripening, vegetable ripening, flower senescence, leaf abscission, seed germination, and the like. In particular embodiments, the plant development process of interest is fruit or vegetable ripening, flower senescence, or leaf abscission, more particularly fruit or vegetable ripening. As defined herein, "delaying a plant development process," and grammatical variants thereof, refers to any slowing, interruption, suppression, or inhibition of the plant development process of interest or the phenotypic or genotypic changes to the plant or plant part typically associated with the specific plant development process. For example, when the plant development process of interest is fruit ripening, a delay in fruit ripening may include inhibition of the changes generally associated with the ripening process (e.g., color change, softening of pericarp (i.e., ovary wall), increases in sugar content, changes in flavor, general degradation/deterioration of the fruit, and eventual decreases in the desirability of the fruit to consumers, as described above). One of skill in the art will appreciate that the length of time required for fruit ripening to occur will vary depending on, for example, the type of fruit and the specific storage conditions utilized (e.g., temperature, humidity, air flow, etc.). Accordingly, "delaying fruit ripening" may constitute a delay of 1 to 90 days, particularly 1 to 30 days, more particularly 5 to 30 days. Methods for assessing a delay in a plant development process such as fruit ripening, vegetable ripening, flower senescence, and leaf abscission are well within the routine capabilities of those of ordinary skill in the art and may be based on, for example, comparison to plant development processes in untreated plants or plant parts. In certain aspects of the invention, delays in a plant development process resulting from the practice of the present methods may be assessed relative to untreated plants or plant parts or to plants or plant parts that have been treated with one or more agents known to retard the plant development process of interest. For example, a delay in fruit ripening resulting from performance of a method of the invention may be compared to fruit ripening times of untreated fruit or fruit that has been treated with an anti-ripening agent, such as those described herein above.

The methods of the invention for delaying a plant development process typically comprise exposing a plant or plant part to one or more of the following bacteria: *Rhodococcus* spp., *Pseudomonas chloroaphis, Brevibacterium ketoglutamicum,* or a mixture containing any combination of these bacteria. In certain embodiments, the one or more bacteria include *Rhodococcus* spp., more particularly *Rhodococcus rhodochrous* DAP 96253 strain, *Rhodococcus* sp. DAP 96622 strain, *Rhodococcus erythropolis*, or mixtures thereof. As used herein, exposing a plant or plant part to one or more of the above bacteria includes, for example, exposure to intact bacterial cells, bacterial cell lysates, and bacterial extracts that possess enzymatic activity (i.e., "enzymatic extracts"). Methods for preparing lysates and enzymatic extracts from cells, including bacterial cells, are routine in the art. The one or more bacteria used in the methods and apparatuses of the invention may at times be more generally referred to herein as the "catalyst."

In accordance with the methods of the invention, the one or more bacteria are exposed to the plant or plant part in a quantity sufficient to delay the plant development process. "Exposing" a plant or plant part to one or more of the bacteria of the invention includes any method for presenting a bacterium to the plant or plant part. Indirect methods of exposure include, for example, placing the bacterium or mixture of bacteria in the general proximity of the plant or plant part (i.e., indirect exposure). In other embodiments, the bacteria may be exposed to the plant or plant part via closer or direct contact. Furthermore, as defined herein, a "sufficient" quantity of the one or more bacteria of the invention will depend on a variety of factors, including but not limited to, the particular bacteria utilized in the method, the form in which the bacteria is exposed to the plant or plant part (e.g., as intact bacterial cells, cell lysates, or enzymatic extracts, as described above), the means by which the bacteria is exposed to the plant or plant part, and the length of time of exposure. It would be a matter of routine experimentation for the skilled artisan to determine the "sufficient" quantity of the one or more bacteria necessary to delay the plant development process of interest.

Although in particular embodiments of the invention the one or more bacteria are selected from the group consisting of *Rhodococcus* spp., *Pseudomonas chloroaphis, Brevibacterium ketoglutamicum*, any bacterium that delays a plant development process when exposed to a plant or plant part can be used in the present methods and apparatuses. For example, bacteria belonging to the genus *Nocardia* [see Japanese Patent Application No. 54-129190], *Rhodococcus* [see Japanese Patent Application No. 2-470], *Rhizobium* [see Japanese Patent Application No. 5-236977], *Klebsiella* [Japanese Patent Application No. 5-30982], *Aeromonas* [Japanese Patent Application No. 5-30983], *Agrobacterium* [Japanese Patent Application No. 8-154691], *Bacillus* [Japanese Patent Application No. 8-187092], *Pseudonocardia* [Japanese Patent Application No. 8-56684], *Pseudomonas*, and *Mycobacterium* are non-limiting examples of microorganisms that can be used according to the invention. Not all species within a given genus may exhibit the same properties. Thus, it is possible to have a genus generally known to include strains capable of exhibiting a desired activity (e.g., the ability to delay a particular plant development process such as, for example, fruit ripening) but have one or more species that do not generally exhibit the desired activity. In light of the disclosure provided herein and the general knowledge in the art, however, it would be a matter of routine experimentation for the skilled artisan to carry out an assay to determine whether a particular species possesses one or more of the desired activities.

Further, specific examples of bacteria useful according to the invention include, but are not limited to, *Nocardia* sp., *Rhodococcus* sp., *Rhodococcus rhodochrous, Klebsiella* sp., *Aeromonas* sp., *Citrobacter freundii, Agrobacterium rhizogenes, Agrobacterium tumefaciens, Xanthobacter flavas, Erwinia nigrifluens, Enterobacter* sp., *Streptomyces* sp., *Rhizobium* sp., *Rhizobium loti, Rhizobium legminosarum, Rhizobium merioti, Candida guilliermondii, Pantoea agglomerans, Klebsiella pneumoniae* subsp. *pneumoniae, Agrobacterium radiobacter, Bacillus smithii, Pseudonocardia thermophila, Pseudomonas chloroaphis, Pseudomonas erythropolis, Brevibacterium ketoglutamicum, Rhodococcus erythropolis, Nocardia farcinica, Pseudomonas aeruginosa,* and *Heliobacter pylori*. In particular embodiments, bacteria from the genus *Rhodococcus*, more specifically *Rhodococcus rhodochrous* DAP 96253 strain (deposited with the ATCC on Dec. 11, 1996), *Rhodococcus* sp. DAP 96622 strain (ATCC Deposit No. 55898; deposited with the ATCC on Dec. 11, 1996), *Rhodococcus erythropolis*, or mixtures thereof, are used in the methods and apparatuses of the invention.

In certain aspects of the invention, the one or more bacteria are "induced" to exhibit a desired characteristic (e.g., the ability to delay a plant development process such as fruit ripening) by exposure to or treatment with a suitable inducing agent. Inducing agents include but are not limited to asparagine, glutamine, cobalt, urea, or any mixture thereof. In particular embodiments, the bacteria are exposed to or treated with the inducing agent asparagine, more particularly a mixture of the inducing agents comprising asparagine, cobalt, and urea. The inducing agent can be added at any time during cultivation of the desired cells. For example, with respect to bacteria, the culture medium can be supplemented with an inducing agent prior to beginning cultivation of the bacteria. Alternately, the bacteria could be cultivated on a medium for a predetermined amount of time to grow the bacteria and the inducing agent could be added at one or more predetermined times to induce the desired enzymatic activity in the bacteria. Moreover, the inducing agent could be added to the growth medium (or to a separate mixture including the previously grown bacteria) to induce the desired activity in the bacteria after the growth of the bacteria is completed.

While not intending to be limited to a particular mechanism, "inducing" the bacteria of the invention may result in the production (or increased production) of one or more enzymes, such as a nitrile hydratase, amidase, and/or asparaginase, and the induction of one or more of these enzymes may play a role in delaying a plant development process of interest. "Nitrile hydratases," "amidases," and "asparaginases" comprise families of enzymes present in cells from various organisms, including but not limited to, bacteria, fungi, plants, and animals. Such enzymes are well known to persons of skill in the art, and each class of enzyme possesses recognized enzymatic activities. "Enzymatic activity," as used herein, generally refers to the ability of an enzyme to act as a catalyst in a process, such as the conversion of one compound to another compound. In particular, nitrile hydratase catalyzes the hydrolysis of nitrile (or cyanohydrin) to the corresponding amide (or hydroxy acid). Amidase catalyzes the hydrolysis of an amide to the corresponding acid or hydroxyl acid. Similarly, an asparaginase enzyme, such as asparaginase I, catalyzes the hydrolysis of asparagine to aspartic acid.

In certain aspects of the invention, enzymatic activity can be referred to in terms of "units" per mass of enzyme or cells (typically based on the dry weight of the cells, e.g., units/mg cdw). A "unit" generally refers to the ability to convert a specific amount of a compound to a different compound under a defined set of conditions as a function of time. In specific embodiments, one "unit" of nitrile hydratase activity can relate to the ability to convert one μmol of acrylonitrile to its corresponding amide per minute, per milligram of cells (dry weight) at a pH of 7.0 and a temperature of 30° C. Similarly, one unit of amidase activity can relate to the ability to convert one μmol of acrylamide to its corresponding acid per minute, per milligram of cells (dry weight) at a pH of 7.0 and a temperature of 30° C. Further, one unit of asparaginase activity can relate to the ability to convert one μmol of asparagine to its corresponding acid per minute, per milligram of cells (dry weight) at a pH of 7.0 and a temperature of 30° C. Assays for measuring nitrile hydratase, amidase activity, or asparaginase activity are known in the art and include, for example, the detection of free ammonia. See Fawcett and Scott (1960) *J. Clin. Pathol.* 13:156-159, which is incorporated herein by reference in their entirety.

Methods of delaying a plant development process comprising exposing a plant or plant part to one or more enzymes selected from the group consisting of nitrile hydratase, amidase, asparaginase, or a mixture thereof, wherein the one or more enzymes are exposed to the plant or plant part in a quantity or at an enzymatic activity level sufficient to delay the plant development process are further encompassed by the present invention. For example, whole cells that produce, are induced to produce, or are genetically modified to produce one or more of the above enzymes (i.e., nitrile hydratase, amidase, and/or asparaginase) may be used in methods to delay a plant development process. Alternatively, the nitrile hydratase, amidase, and/or asparaginase may be isolated, purified, or semi-purified from any the above cells and exposed to the plant or plant part in a more isolated form. See, for example, Goda et al. (2001) *J. Biol. Chem.* 276:23480-23485; Nagasawa et al. (2000) *Eur. J. Biochem.* 267:138-144; Soong et al. (2000) *Appl. Environ. Microbiol.* 66:1947-1952; Kato et al. (1999) *Eur. J. Biochem.* 263:662-670, all of which are herein incorporated by reference in their entirety. One of skill in the art will further appreciate that a single cell type may be capable of producing (or being induced or genetically modified to produce) more than one of the enzymes of the invention. Such cells are suitable for use in the disclosed methods and apparatuses.

The nucleotide and amino acid sequences for several nitrile hydratases, amidases, and asparaginases from various organisms are disclosed in publicly available sequence databases. A non-limiting list of representative nitrile hydratases and aliphatic amidases known in the art is set forth in Tables 1 and 2 and in the sequence listing. The "protein score" referred to in Tables 1 and 2 provides an overview of percentage confidence intervals (% Confid. Interval) of the identification of the isolated proteins based on mass spectroscopy data.

TABLE 1

Amino Acid Sequence Information for Representative Nitrile Hydratases

| Source organism | Accession No. | Sequence Identifier | Protein Score (% Confid. Interval) |
|---|---|---|---|
| *Rhodococcus* sp. | 806580 | SEQ ID NO: 1 | 100% |
| *Nocardia* sp. | 27261874 | SEQ ID NO: 2 | 100% |
| *Rhodococcus rhodochrous* | 49058 | SEQ ID NO: 3 | 100% |

TABLE 1-continued

Amino Acid Sequence Information for Representative Nitrile Hydratases

| Source organism | Accession No. | Sequence Identifier | Protein Score (% Confid. Interval) |
|---|---|---|---|
| Uncultured bacterium (BD2); beta-subunit of nitrile hydratase | 27657379 | SEQ ID NO: 4 | 100% |
| *Rhodococcus* sp. | 806581 | SEQ ID NO: 5 | 100% |
| *Rhodococcus rhodochrous* | 581528 | SEQ ID NO: 6 | 100% |
| Uncultured bacterium (SP1); alpha-subunit of nitrile hydratase | 7657369 | SEQ ID NO: 7 | 100% |

TABLE 2

Amino Acid Sequence Information for Representative Aliphatic Amidases

| Source organism | Accession No. | Sequence Identifier | Protein Score (% Confid. Interval) |
|---|---|---|---|
| *Rhodococcus rhodochrous* | 62461692 | SEQ ID NO: 8 | 100% |
| *Nocardia farcinica* IFM 10152 | 54022723 | SEQ ID NO: 9 | 100% |
| *Pseudomonas aeruginosa* PAO1 | 15598562 | SEQ ID NO: 10 | 98.3% |
| *Helicobacter pylori* J99 | 15611349 | SEQ ID NO: 11 | 99.6% |
| *Helicobacter pylori* 26695 | 2313392 | SEQ ID NO: 12 | 97.7% |
| *Pseudomonas aeruginosa* | 150980 | SEQ ID NO: 13 | 94% |

Generally, any bacterial, fungal, plant, or animal cell capable of producing or being induced to produce nitrile hydratase, amidase, asparaginase, or any combination thereof may be used in the practice of the invention. A nitrile hydratase, amidase, and/or asparaginase may be produced constitutively in a cell from a particular organism (e.g., a bacterium, fungus, plant cell, or animal cell) or, alternatively, a cell may produce the desired enzyme or enzymes only following "induction" with a suitable inducing agent. "Constitutively" is intended to mean that at least one enzyme of the invention is continually produced or expressed in a particular cell type. Other cell types, however, may need to be "induced," as described above, to express nitrile hydratase, amidase, and/or asparaginase at a sufficient quantity or enzymatic activity level to delay a plant development process of interest. That is, an enzyme of the invention may only be produced (or produced at sufficient levels) following exposure to or treatment with a suitable inducing agent. Such inducing agents are known in the art and outlined above. For example, in certain aspects of the invention, the one or more bacteria are treated with an inducing agent such as asparagine, glutamine, cobalt, urea, or any mixture thereof, more particularly a mixture of asparagine, cobalt, and urea. Furthermore, as disclosed in pending U.S. application Ser. No. 11/669,011, entitled "Induction and Stabilization of Enzymatic Activity in Microorganisms," filed Jan. 30, 2007, asparaginase I activity can be induced in *Rhodococcus rhodochrous* DAP 96622 (Gram-positive) or *Rhodococcus* sp. DAP 96253 (Gram-positive), in medium supplemented with amide containing amino acids, or derivatives thereof. Other strains of *Rhodococcus* can also preferentially be similarly induced to exhibit asparaginase I enzymatic activity utilizing amide containing amino acids, or derivatives thereof.

In other aspects of the invention, *P. chloroaphis*, which produces asparaginase I activity in the presence of asparagine, and *B. kletoglutamicum*, a Gram-positive bacterium that has also been shown to produce asparaginase activity, are used in the disclosed methods. Fungal cells, such as those from the genus *Fusarium*, plant cells, and animal cells, that express a nitrile hydratase, amidase, and/or an asparaginase, may also be used in the methods and apparatuses disclosed herein, either as whole cells or as a source from which to isolated one or more of the above enzymes.

In additional embodiments, host cells that have been genetically engineered to express a nitrile hydratase, amidase, and/or asparaginase can be used exposed to a plant or plant part in accordance with the present methods and apparatuses for delaying a plant development process. Specifically, a polynucleotide that encodes a nitrile hydratase, amidase, or asparaginase (or multiple polynucleotides each of which encodes a nitrile hydratase, amidase, or asparaginase) may be introduced by standard molecular biology techniques into a host cell to produce a transgenic cell that expresses one or more of the enzymes of the invention. The use of the terms "polynucleotide," "polynucleotide construct," "nucleotide," or "nucleotide construct" is not intended to limit the present invention to polynucleotides or nucleotides comprising DNA. Those of ordinary skill in the art will recognize that polynucleotides and nucleotides can comprise ribonucleotides and combinations of ribonucleotides and deoxyribonucleotides. Such deoxyribonucleotides and ribonucleotides include both naturally occurring molecules and synthetic analogues. The polynucleotides of the invention also encompass all forms of sequences including, but not limited to, single-stranded forms, double-stranded forms, and the like.

Variants and fragments of polynucleotides that encode polypeptides that retain the desired enzymatic activity (i.e., nitrile hydratase, amidase, or asparaginase activity) may also be used in the practice of the invention. By "fragment" is intended a portion of the polynucleotide and hence also encodes a portion of the corresponding protein. Polynucleotides that are fragments of an enzyme nucleotide sequence generally comprise at least 10, 15, 20, 50, 75, 100, 150, 200, 250, 300, 350, 400, 450, 500, 550, 600, 650, 700, 800, 900, 1,000, 1,100, 1,200, 1,300, or 1,400 contiguous nucleotides, or up to the number of nucleotides present in a full-length enzyme polynucleotide sequence. A polynucleotide fragment will encode a polypeptide with a desired enzymatic activity and will generally encode at least 15, 25, 30, 50, 100, 150, 200, or 250 contiguous amino acids, or up to the total number of amino acids present in a full-length enzyme amino acid sequence of the invention. "Variant" is intended to mean substantially similar sequences. Generally, variants of a particular enzyme sequence of the invention will have at least about 40%, 45%, 50%, 55%, 60%, 65%, 70%, 75%, 80%, 85%, 90%, 91%, 92%, 93%, 94%, 95%, 96%, 97%, 98%, 99% or more sequence identity to the reference enzyme sequence, as determined by standard sequence alignment programs. Variant polynucleotides encompassed by the invention will encode polypeptides with the desired enzyme activity.

As used in the context of production of transgenic cells, the term "introducing" is intended to mean presenting to a host cell, particularly a microorganism such as *Escherichia coli*, with a polynucleotide that encodes a nitrile hydratase, amidase, and/or asparaginase. In some embodiments, the polynucleotide will be presented in such a manner that the sequence gains access to the interior of a host cell, including its potential insertion into the genome of the host cell. The methods of the invention do not depend on a particular method for introducing a sequence into a host cell, only that the polynucleotide gains access to the interior of at least one host cell. Methods for introducing polynucleotides into host cells are well known in the art including, but not limited to, stable transfection methods, transient transfection methods, and virus-mediated methods. "Stable transfection" is intended to mean that the polynucleotide construct introduced into a host cell integrates into the genome of the host and is capable of being inherited by the progeny thereof. "Transient transfection" or "transient expression" is intended to mean that a polynucleotide is introduced into the host cell but does not integrate into the host's genome.

Furthermore, the nitrile hydratase, amidase, or asparaginase nucleotide sequence may be contained on, for example, a plasmid for introduction into the host cell. Typical plasmids of interest include vectors having defined cloning sites, origins of replication, and selectable markers. The plasmid may further include transcription and translation initiation sequences and transcription and translation terminators. Plasmids can also include generic expression cassettes containing at least one independent terminator sequence, sequences permitting replication of the cassette in eukaryotes, or prokaryotes, or both, (e.g., shuttle vectors) and selection markers for both prokaryotic and eukaryotic systems. Vectors are suitable for replication and integration in prokaryotes, eukaryotes, or optimally both. For general descriptions of cloning, packaging, and expression systems and methods, see Giliman and Smith (1979) *Gene* 8:81-97; Roberts et al. (1987) *Nature* 328:731-734; Berger and Kimmel (1989) *Guide to Molecular Cloning Techniques, Methods in Enzymology*, Vol. 152 (Academic Press, Inc., San Diego, Calif.); Sambrook et al. (1989) *Molecular Cloning: A Laboratory Manual*, Vols. 1-3 (2d ed; Cold Spring Harbor Laboratory Press, Plainview, N.Y.); and Ausubel et al., eds. (1994) *Current Protocols in Molecular Biology, Current Protocols* (Greene Publishing Associates, Inc., and John Wiley & Sons, Inc., New York; 1994 Supplement). Transgenic host cells that express one or more of the enzymes of the invention may be used in the disclosed methods and apparatuses as whole cells or as a biological source from which one or more enzymes of the invention can be isolated.

Apparatuses for delaying a plant development process and for performing the methods of the invention are further provided. In particular embodiments, an apparatus for delaying a plant development process, particularly fruit ripening, comprising a catalyst that comprises one or more bacteria selected from the group consisting of *Rhodococcus* spp., *Pseudomonas chloroaphis, Brevibacterium ketoglutamicum*, and mixtures thereof is encompassed by the present invention. *Rhodococcus rhodochrous* DAP 96253 strain, *Rhodococcus* sp. DAP 96622 strain, *Rhodococcus erythropolis*, or mixtures thereof may be used in certain aspects of the invention. The one or more bacteria of an apparatus of the invention are provided in a quantity sufficient to delay a plant development process of interest, as defined herein above. In other aspects of the invention, the catalyst comprises one or more enzymes (i.e., nitrile hydratase, amidase, and/or asparaginase) in a quantity or at an enzymatic activity level sufficient to delay a plant development process. Sources of the desired enzymes for use as a catalyst in the apparatuses of the invention are also described in detail above. For example, the catalyst may be used in the form of whole cells that produce (or are induced or genetically modified to produce) one or more of the enzymes of the invention or may comprise the enzyme(s) themselves in an isolated, purified, or semi-purified form.

Apparatuses for delaying a plant development process encompassed by the present invention may be provided in a variety of suitable formats and may be appropriate for single use or multiple uses (e.g., "re-chargeable"). Furthermore, the apparatuses of the invention find use in both residential and commercial settings. For example, such apparatuses can be integrated into residential or commercial refrigerators, included in trains, trucks, etc. for long-distance transport of fruit, vegetables, or flowers, or used as stand-alone cabinets for the storage or transport of such plant products. Exemplary, non-limiting apparatuses of the invention are described herein below and depicted in FIGS. 1-4.

In particular embodiments, the catalyst is provided in an immobilized format. Any process or matrix for immobilizing the catalyst may be used so long as the ability of the one or more bacteria (or enzymes) to delay a plant development process is retained. For example, the catalyst may be immobilized in a matrix comprising alginate (e.g., calcium alginate), carrageen, DEAE-cellulose, or polyacrylamide. Other such matrices are well known in the art and may be further cross-linked with any appropriate cross-linking agent, including but not limited to glutaraldehyde or polyethylenimine, to increase the mechanical strength of the catalyst matrix. In one aspect of the invention, the catalyst is immobilized in a glutaraldehyde cross-linked DEAE-cellulose matrix. The catalyst, particularly the catalyst in an immobilized form, may be further presented as a "catalyst module element." A catalyst module element comprises a catalyst, such as an immobilized catalyst, within an additional structure that, for example, reduces potential contact with the catalyst, facilitates replacement of the catalyst, or permits air flow across the catalyst.

In one embodiment, the matrix comprises alginate, or salts thereof. Alginate is a linear copolymer with homopolymeric blocks of (1-4)-linked β-D-mannuronate (M) and its C-5 epimer α-L-guluronate (G) residues, respectively, covalently linked together in different sequences or blocks. The monomers can appear in homopolymeric blocks of consecutive G-residues (G-blocks), consecutive M-residues (M-blocks), alternating M and G-residues (MG-blocks), or randomly organized blocks. In one embodiment, calcium alginate is used as the substrate, more particularly calcium alginate that has been cross-linked, such as with polyethylenimine, to form a hardened calcium alginate substrate. Further description of such immobilization techniques can be found in Bucke (1987) "Cell Immobilization in Calcium Alginate" in *Methods in Enzymology*, Vol. 135(B) (Academic Press, Inc., San Diego, Calif.; Mosbach, ed.), which is incorporated herein by reference. An exemplary method of immobilization using polyethyleneimine cross-linked calcium alginate is also described below in Example 5. In another embodiment, the matrix comprises an amide-containing polymer. Any polymer comprising one or more amide groups could be used according to the invention. In one embodiment, the substrate comprises a polyacrylamide polymer.

Increased mechanical strength of an immobilized catalyst matrix can be achieved through cross-linking. For example, cells can be chemically cross-linked to form agglutinations of cells. In one embodiment, cells harvested are cross-linked using glutaraldehyde. For example, cells can be suspended in a mixture of de-ionized water and glutaraldehyde followed by addition of polyethyleneimine until maximum flocculation is achieved. The cross-linked cells (typically in the form of particles formed of a number of cells) can be harvested by simple filtration. Further description of such techniques is provided in Lopez-Gallego et al. (2005) *J. Biotechnol.* 119: 70-75, which is hereby incorporated by reference in its entirety. A general protocol for immobilization of cells, particularly *Rhodococcus* spp. cells, in DEAE-cellulose cross-linked with glutaraldehyde is also outlined below in Example 4.

In certain aspects of the invention, the immobilized catalyst or one or more catalyst module elements are placed in, placed on, or affixed to a "physical structure." The physical structure includes but is not limited to a film, sheet, coating layer, box, pouch, bag, or slotted chamber capable of holding one or more catalyst module elements. In certain embodiments, the physical structure comprises a container suitable for transport or storage of fruit, vegetables, or flowers. The physical structure may further comprise more than one individual structure, whereby all of the individual structures are connected to a central catalyst or catalyst module element. A physical structure described herein above may optionally be refrigerated by external means or comprise a refrigeration unit within the physical structure itself.

Elements for monitoring the efficacy of the catalyst for delaying a plant development process of interest (e.g., to assess when the catalyst or catalyst module should be replaced) or for measuring or controlling air flow, moisture content/humidity, and carbon dioxide levels may be optionally included in an apparatus of the invention. Any apparatus for delaying a plant development process may further comprise one or more elements to permit air flow to or through the catalyst or catalyst module element. The skilled artisan would readily envision other possible modifications to the apparatuses described herein for monitoring and controlling the atmospheric conditions (e.g., air flow, humidity, and carbon dioxide levels) of the catalyst, the catalyst module element, or the physical structure. Conditions such as temperature, atmospheric composition (e.g., relative humidity, $O_2$ and $CO_2$ levels, physical stress, light, chemical stress, radiation, water stress, growth regulators, and pathogen attack play an important role in respiration rates and significantly impact shelf-life of fruits, vegetables, flowers, and other plant-related products. Although temperature and atmospheric conditions for storage vary depending on the fruit, vegetable, or other plant product of interest, recommended storage temperatures are typically in the range of about 0° to about 20° C. with $O_2$ and $CO_2$ levels in the approximate ranges of 1-10% and 0-20%, respectively. A relative humidity of about 50% to about 100%, particularly 85% to about 95%, more particularly about 90% to about 95% is generally recommended for the storage of fruits, vegetables, and related plant products. Given the significant correlation between respiration rate and shelf-life of plant products, control of the above factors is important to delaying the deterioration of such products. Accordingly, a carbon dioxide scavenger can be provided in the apparatus to reduce the carbon dioxide content.

In particular embodiments of the invention, air-permeable catalyst apparatuses for delaying a plant development process comprising multiple layers are provided. For example, as shown in FIG. 1, a catalyst apparatus 10 can include outer layers 12 and 14 and an intermediate catalyst layer 16 located between the outer layers 12 and 14. The catalyst layer 16 comprises one or more bacteria (e.g., *Rhodococcus* spp., *Pseudomonas chloroaphis, Brevibacterium ketoglutamicum*, and mixtures thereof) or enzymes (a nitrile hydratase, amidase, asparaginase, and mixtures thereof), wherein the one or more bacteria or enzymes are provided in a quantity sufficient to delay the plant development process of interest, and a third layer. In this embodiment, one or more of the outer layers 12 and 14 provide structural integrity to the catalyst apparatus 10. The outer layers 12 and 14 typically permit air flow to the catalyst layer 16 although, in some embodiments, it may be advantageous to have an outer layer that is not air-permeable, e.g., if apparatus forms the side of the box and there is a desire not to allow the outermost layer of the box to expose the catalyst layer to the environment. The catalyst apparatus 10 can be provided in reusable or non-reusable bags or pouches in accordance with the invention. In one embodiment, the catalyst layer 16 comprises *Rhodococcus* spp. cells, particularly *Rhodococcus rhodochrous* DAP 96253 strain, *Rhodococcus* sp. DAP 96622 strain, *Rhodococcus erythropolis*, or mixtures thereof. Bacterial cells utilized as a catalyst in an apparatus of the invention may be induced with one or more inducing agents (e.g., asparagine, glutamine, cobalt, urea, or a mixture thereof), as described in detail above.

FIGS. 2A-2C illustrate alternative apparatuses in accordance with the invention for delaying a plant development process. These apparatuses comprise multiple layers, wherein one or more of the layers are removable. As shown in FIG. 2A, the apparatus can include an air-permeable structural layer 22 and a catalyst layer 24. Removable layers 26 and/or 28 can be provided along the structural layer 22 and/or the catalyst layer 24 and are typically intended to be removed prior to using or activating the catalyst. In certain aspects of the invention, the removal of the removable layers 26 and 28 expose an adhesive that facilitates placement or attachment of the catalyst structure to a separate physical structure. FIG. 2B illustrates an alternative embodiment wherein the apparatus 30 includes two air-permeable structural layers 32 and 34, an intermediate catalyst layer 36 and a removable layer 38. FIG. 2C illustrates yet another embodiment wherein the apparatus 40 includes two air-permeable structural layers 42 and 44, an intermediate catalyst layer 46 and two removable layers 48 and 50.

FIGS. 3A-3B illustrate an alternative embodiment 60 wherein the catalyst is affixed to the interior of a container such as a cardboard box. As shown in FIG. 3A, a side 62 of the container includes a catalyst layer 64 attached thereto through the use of an adhesive layer 66. A peelable film 68 can be provided adjacent the catalyst layer 64 to protect the catalyst layer from exposure to the environment. The peelable film 68 can be removed to activate the catalyst in the catalyst layer 64 by exposing the catalyst to a plant part provided in the container to thereby delay an undesired plant development process.

FIG. 3B illustrates a catalyst structure 70 prior to affixing the catalyst structure to a container interior in the manner shown in FIG. 3A. In addition to the catalyst layer 64, the adhesive layer 66, and the peelable film 68, the catalyst structure 70 includes an additional peelable film 72. The peelable film 72, like the peelable film 68, protects the catalyst structure 70 when it is packaged, shipped or stored. The peelable film 72 can be removed to expose the adhesive layer 66 to allow the catalyst structure 70 to be affixed to the container interior in the manner illustrated in FIG. 3A.

FIG. 4 illustrates a catalyst structure 80 that includes two slots 82 and 84 for receiving a catalyst cassette (e.g. cassette 86). The catalyst cassette 86 is air-permeable and can be easily inserted into or removed from slot 84. Thus, the catalyst cassette 86 can be readily replaced if a new catalyst cassette is desired for use in the catalyst structure 80. The catalyst cassette 86 includes a catalyst such as described herein and that is preferably immobilized in a matrix. The catalyst structure 80 can include opposed air-permeable surfaces 88 and 90 such as mesh screens to allow air flow through the catalyst cassette 86. The catalyst structure 80 can, in alternative embodiments, include only one air-permeable surface, two non-opposed air-permeable surfaces or more than two air-permeable surfaces as would be understood to one of skill in the art. Although FIG. 4 includes two slots 82 and 84 for receiving a catalyst cassette (e.g. cassette 86), it would be understood to one of skill in the art that the catalyst structure 80 could include one or more slots for receiving a cassette. The catalyst structure 80 can be provided within a container used to transport a plant part such as fruit or flowers or can be affixed to a container, e.g., through the use of an adhesive layer as discussed herein.

The present methods and apparatuses may be used to delay a plant development process of any plant or plant part of interest. In particular embodiments, the methods and apparatuses of the invention are directed to delaying ripening and the plant part is a fruit (climacteric or non-climacteric), vegetable, or other plant part subject to ripening. One of skill in the art will recognize that "climacteric fruits" exhibit a sudden burst of ethylene production during fruit ripening, whereas "nonclimacteric fruits" are generally not believed to experience a significant increase in ethylene biosynthesis during the ripening process. Exemplary fruits, vegetables, and other plant products of interest include but are not limited to: apples, apricots, biriba, breadfruit, cherimoya, feijoa, fig, guava, jackfruit, kiwi, bananas, peaches, avocados, apples, cantaloupes, mangos, muskmelons, nectarines, persimmon, sapote, soursop, olives, papaya, passion fruit, pears, plums, tomatoes, bell peppers, blueberries, cacao, caju, cucumbers, grapefruit, lemons, limes, peppers, cherries, oranges, grapes, pineapples, strawberries, watermelons, tamarillos, and nuts.

In other aspects of the invention, the methods and apparatuses are drawn to delaying flower senescence, wilting, abscission, or petal closure. Any flower may be used in the practice of the invention. Exemplary flowers of interest include but are not limited to roses, carnations, orchids, portulaca, malva, and begonias. Cut flowers, more particularly commercially important cut flowers such as roses and carnations, are of particular interest. In certain embodiments, flowers that are sensitive to ethylene are used in the practice of the invention. Ethylene-sensitive flowers include but are not limited to flowers from the genera *Alstroemeria, Aneomone, Anthurium, Antirrhinum, Aster, Astilbe, Cattleya. Cymbidium, Dahlia, Dendrobium, Dianthus, Eustoma, Freesia, Gerbera, Gypsophila, Iris, Lathyrus, Lilium, Limonium, Nerine, Rosa, Syringa, Tulipa,* and *Zinnia*. Representative ethylene-sensitive flowers also include those of the families Amarylidaceae, Alliaceae, Convallariaceae, Hemerocallidaceae, Hyacinthaceae, Liliaceae, Orchidaceae, Aizoaceae, Cactaceae, Campanulaceae, Caryophyllaceae, Crassulaceae, Gentianaceae, Malvaceae, Plumbaginaceae, Portulacaceae, Solanaceae, Agavacaea, Asphodelaceae, Asparagaceae, Begoniaceae, Caprifoliaceae, Dipsacaceae, Euphorbiaceae, Fabaceae, Lamiaceae, Myrtaceae, Onagraceae, Saxifragaceae, and Verbenaceae. See, for example, Van Doom (2002) Annals of Botany 89:375-383; Van Doom (2002) Annals of Botany 89:689-693; and Elgar (1998) "Cut Flowers and Foliage—Cooling Requirements and Temperature Management" at hortnet.co.nz/publications/hortfacts/hf305004.htm (last accessed Mar. 20, 2007), all of which are herein incorporated by reference in their entirety. Methods and apparatuses for delaying leaf abscission are also encompassed by the present invention. Significant commercial interest exists in the plant, fruit, vegetable, and flower industries for methods and apparatuses for regulating plant development processes such as ripening, senescence, and abscission.

The skilled artisan will further recognize that any of the methods or apparatuses disclosed herein can be combined with other known methods and apparatuses for delaying a plant development process, particularly those processes generally associated with increased ethylene biosynthesis (e.g., fruit/vegetable ripening, flower senescence, and leaf abscission). Moreover, as described above, increased ethylene production has also been observed during attack of plants or plant parts by pathogenic organisms. Accordingly, the methods and apparatuses of the invention may find further use in improving plant response to pathogens.

The following examples are offered by way of illustration and not by way of limitation:

EXPERIMENTAL

The present invention will now be described with specific reference to various examples. The following examples are not intended to be limiting of the invention and are rather provided as exemplary embodiments.

Example 1

Delayed Fruit Ripening Following Exposure to Induced *Rhodococcus* spp.

*Rhodococcus* spp. cells induced with asparagine, acrylonitrile, or acetonitrile were immobilized in a glutaraldehyde-cross-linked matrix of DEAE-cellulose. Methods of inducing cells and preparing the above matrix are described herein below in greater detail.

The cross-linked DEAE-cellulose catalyst matrix was placed in three separate paper bags (approximately 1-2 grams pack wet weight of cells per bag), with each bag containing unripe bananas, peaches, or avocados. As negative controls, the same fruits were placed in separate paper bags in the absence of the catalyst matrix. The paper bags were retained at room temperature, and the produce was observed daily for signs of fruit ripening and degradation.

All produce exposed to the catalyst matrix displayed significant delays in fruit ripening. In particular, the firmness and skin integrity of the peaches was maintained longer in the presence of the catalyst matrix. Similarly, with the bananas, the appearance of brown spots was delayed and the firmness retained longer relative to the negative controls.

Example 2

General Fermentation and Induction Protocols

Fermentation Process

The following general protocols and culture media were utilized for fermentation of the *Rhodococcus* spp. strains *Rhodococcus* sp. DAP 96622 and *Rhodococcus rhodochrous* DAP 96253 for use in other experiments:

Fermentation vessels were configured with probes to measure dissolved oxygen (DO) and pH, as well as with sampling devices to measure glucose concentration (off-line). Additional ports were used to add correctives (e.g., acid, base, or antifoam), inducers, nutrients and supplements. Previously cleaned vessels were sterilized in-place. A suitable base medium (1 or 1.5×) R2A or R3A was used. The specific components of these culture media are set forth below. Certain substitutions to the contents of the media were made in certain experiments. For example, Proflo® (Trader's Protein, Memphis, Tenn.) was at times used in place of the proteose peptone and/or casamino acids. Moreover, in certain experiments, Hy-Cotton 7803 ® (Quest International, Hoffman Estates, IL), Cottonseed Hydrolysate, Cottonseed Hydrolysate-Ultrafiltered (Marcor Development Corp., Carlstadt, N.J.) was used in place of the Proflo® (Trader's Protein, Memphis, Tenn.).

A feed profile for nutrient supplementation was set to gradually replace the R2A or R3A base medium with a richer medium, namely 2×YEMEA, the components of which are also described in greater detail below. Other optional nutrient supplements included maltose 50% (w/v) and dextrose 50% (w/v). Commercial products containing dextrose equivalents (glucose, maltose, and higher polysaccharides) were sometimes used in place of maltose and dextrose.

Inocula were prepared from cultures of the *Rhodococcus* sp. DAP 96622 and *Rhodococcus rhodochrous* DAP 96253 strains on a suitable solid medium and incubated at their appropriate temperature (e.g., 30° C.). In particular embodiments, cells were grown on YEMEA agar plates for 4-14 days, preferably 7 days. Alternatively, inocula were prepared from frozen cell concentrates from previous fermentation runs. Cell concentrates were typically prepared at a 20× concentration over that present in the fermentor. In addition, inoculum was at times prepared from a suitable biphasic medium (i.e., a combination of liquid medium overlaying a solid medium of the same or different composition). When a biphasic medium was used, the medium generally contained YEMEA in both the liquid and solid layers.

For induction of nitrile hydratase, at t=0 hour, sterile $CoCl_2 \cdot 6H_2O$ and urea were added to achieve concentrations of 5-200 ppm of $CoCl_2$ and 750 mg/1-10 g/l of urea, with 10-50 ppm $CoCl_2$ and 7500 mg/1-7.5 g/l urea generally preferred. In a particular embodiment, urea and/or cobalt were added again during the fermentation. For example, an equivalent volume of urea and 150 ppm $CoCl_2$ were added at 4-6 hours or at 24-30 hours. In addition to urea, a final concentration of 300-500 ppm of acrylonitrile/acetonitrile or 0.1 M-0.2 M asparagine was added step-wise or at a constant rate, beginning at various times. The fermentation runs were terminated when cell mass and enzyme concentrations were acceptable, typically at 24-96 hours.

The cells were then harvested by any acceptable method, including but not limited to batch or continuous centrifugation, decanting, or filtration. Harvested cells were resuspended to a 20× concentrated volume in a suitable buffer such as 50 mM phosphate buffered saline (PBS) supplemented with the inducer used during the fermentation process. Cell concentrates were then frozen, particularly by rapid freezing. Frozen cells were stored at −20° C.–80° C. or under liquid nitrogen for later use.

Description of Culture Media

| R2A Medium (See Reasoner and Geldreich (1985) Appl. Environ. Microbiol. 49: 1-7.) | |
|---|---|
| Yeast Extract | 0.5 g |
| Proteose Peptone #3 | 0.5 g |
| Casamino acids | 0.5 g |
| Glucose | 0.5 g |
| Soluble starch | 0.5 g |
| $K_2HPO_4$ | 0.3 g |
| $MgSO_4 \cdot 7H_2O$ | 0.05 g |
| Sodium Pyruvate | 0.3 g |
| DI or dist $H_2O$ | 1.0 liter |

| R3A Medium (See Reasoner and Geldreich, supra.) | |
|---|---|
| Yeast Extract | 1.0 g |
| Proteose Peptone #3 | 1.0 g |
| Casamino acids | 1.0 g |

-continued

| R3A Medium (See Reasoner and Geldreich, supra.) | |
|---|---|
| Glucose | 1.0 g |
| Soluble starch | 1.0 g |
| $K_2HPO_4$ | 0.6 g |
| $MgSO_4 \cdot 7H_2O$ | 0.1 g |
| Sodium Pyruvate | 0.5 g |
| DI or dist $H_2O$ | 1.0 liter |

| YEMEA Medium | | |
|---|---|---|
| | 1X | 2X |
| Yeast Extract | 4.0 g | 8.0 g |
| Malt Extract | 10.0 g | 20.0 g |
| Glucose | 4.0 g | 8.0 g |
| DI or dist $H_2O$ | 1.0 liter | 1.0 liter |

Induction

The following general protocol was utilized for induction of the *Rhodococcus* spp. strains *Rhodococcus* sp. DAP 96622 and *Rhodococcus rhodochrous* DAP 96253:

Volatile inducer liquids (e.g., acrylonitrile/acetonitrile) were added volumetrically as filter-sterilized liquid inducers based upon the density of the particular liquid inducer. In the case of solid inducers (e.g., asparagine/glutamine), the solids were weighed and added directly to the culture medium. The resulting media were autoclaved. When filter-sterilized liquid inducers were utilized, the culture medium alone was autoclaved and cooled to 40° C. before the liquid inducer was added. Typical concentrations for inducers of interest were: 500 ppm acrylonitrile/acetonitrile; 500 ppm asparagine/glutamine; and 50 ppm succinonitrile. Cells were then grown on specified media and further analyzed for particular enzymatic activities and biomass.

Example 3

Analysis of Nitrile Hydratase, Amidase, and Asparaginase Activity and Biomass in Asparagine-Induced *Rhodococcus* spp. Cells Nitrile hydratase, amidase, and asparaginase activity and biomass were assessed in asparagines-induced cells from the *Rhodococcus* spp. strains *Rhodococcus* sp. DAP 96622 and *Rhodococcus rhodochrous* DAP 96253. Various modifications to culture media components, the administration methods, rates, and concentrations of asparagine provided to the cells, and the source of the cells were analyzed with respect to their effects on the activities of the above enzymes and on biomass. Sections A through G of this Example describe the specifics of each set of test conditions and provide a summary of the enzymatic activities and biomasses obtained under each the specified conditions.

A. Essentially as described above in Example 2, a 20-liter fermentor inoculated using cells of *Rhodococcus rhodochrous* DAP 96253 harvested from solid medium was continuously supplemented with the inducer asparagine (120 μl/minute of a 0.2 M solution). Hy-Cotton 7803® was used in place of the proteose peptone #3 in the R3A medium described above. At the end of the fermentation run, acrylonitrile-specific nitrile hydratase activity, amidase activity, and biomass were measured in accordance with standard techniques known in the art.

The results for nitrile hydratase activity, amidase activity, and biomass are provided below in Table 3, with activities provided in units/mg cdw (cell dry weight). One unit of nitrile hydratase activity relates to the ability to convert 1 μmol of acrylonitrile to its corresponding amide per minute, per milligram of cells (dry weight) at pH 7.0 and a temperature of 30° C. One unit of amidase activity relates to the ability to convert 1 μmol of acrylamide to its corresponding acid per minute, per milligram of cells (dry weight) pH of 7.0 and a temperature of 30° C. Biomass is reported as cells packed in g/l cww (cell wet weight).

TABLE 3

Enzymatic Activities and Biomass of *Rhodococcus rhodochrous* DAP 96253 Cells Following Induction with Asparagine

| Nitrile Hydratase Activity (Units/mg cdw) | Amidase Activity (Units/mg cdw) | Biomass (g/l cww) |
|---|---|---|
| 168 | 2 | 36 |

B. Essentially as described above in Example 3A, with changes to the medium as noted below, enzymatic activities and biomass were assessed with *Rhodococcus rhodochrous* DAP 96253 cells. In particular, YEMEA, dextrose or maltose was added to a modified R3A medium, further containing Hy-Cotton 7803® substituted for the proteose peptone #3. A 0.2 M solution of asparagine was added at a continuous rate of 120 μl/minute beginning at t=8 hours. At the end of the fermentation run, acrylonitrile-specific nitrile hydratase activity, amidase activity, and biomass were measured. Results are summarized in Table 4. Increased biomass yield was observed with the addition of YEMEA, dextrose, or maltose to the medium.

TABLE 4

Enzymatic Activities and Biomass of *Rhodococcus rhodochrous* DAP 96253 Cells Following Continuous Induction with Asparagine

| Nitrile Hydratase Activity (Units/mg cdw) | Amidase Activity (Units/mg cdw) | Biomass (g/l cww) |
|---|---|---|
| 155 | 6 | 52 |

C. *Rhodococcus* sp. DAP 96622 cells from solid medium were used as the source of the inoculum for a 20-liter fermentation run (see Example 2 for details of fermentation process). A 0.2 M solution of asparagine was added semi-continuously every 6 hours, beginning at t=24 hours, for 50-70 minutes at a rate of 2 ml/minute. Hy-Cotton 7803® was used in place of the proteose peptone #3 in a modified R3A medium. At the end of the fermentation run, acrylonitrile-specific nitrile hydratase activity, amidase activity, and biomass were measured. The results are summarized in Table 5.

TABLE 5

Enzymatic Activities and Biomass of *Rhodococcus* sp. DAP 96622 Cells Following Semi-Continuous Induction with Asparagine

| Nitrile Hydratase Activity (Units/mg cdw) | Amidase Activity (Units/mg cdw) | Biomass (g/l cww) |
|---|---|---|
| 172 | 2 | 44 |

D. *Rhodococcus* sp. DAP 96622 cells from solid medium were used as the source of the inoculum for a 20-liter fermentor run. A 0.2 M solution of asparagine was added semi-continuously every 6 hours, beginning at t=12 hours, for 12-85 minutes at a rate of 2.5 ml/minute. Cotton Seed Hydrolysate was used in place of the proteose peptone #3 in a modified R3A medium. At the end of the fermentation run, acrylonitrile-specific nitrile hydratase activity, amidase activity, and biomass were measured, and the results are summarized in Table 6.

TABLE 6

Enzymatic Activities and Biomass of *Rhodococcus* sp. DAP 96622 Cells Following Semi-Continuous Induction with Asparagine

| Nitrile Hydratase Activity (Units/mg cdw) | Amidase Activity (Units/mg cdw) | Biomass (g/l cww) |
|---|---|---|
| 165 | 2 | 57 |

E. Previously frozen *Rhodococcus rhodochrous* DAP 96253 cells were used as the source of the inoculum for a 20-liter fermentation run. YEMEA, dextrose, or maltose was added to a modified R3A medium that further contained Hy-Cotton 7803® as a substitute for proteose peptone #3. A 0.15 M solution of asparagine was added at a continuous rate of 120 μl/minute beginning at t=8 hours. At the end of the fermentation run, acrylonitrile-specific nitrile hydratase activity, amidase activity, and biomass were measured. Results are summarized in Table 7.

TABLE 7

Enzymatic Activities and Biomass of *Rhodococcus rhodochrous* DAP 96253 Cells Following Continuous Induction with Asparagine

| Nitrile Hydratase Activity (Units/mg cdw) | Amidase Activity (Units/mg cdw) | Biomass (g/l cww) |
|---|---|---|
| 171 | 4 | 74 |

F. *Rhodococcus rhodochrous* DAP 96253 cells grown on biphasic medium were used as the source of inoculum for a 20-liter fermentation run. A modified R3A medium was used that was supplemented by the addition of a carbohydrate (i.e., YEMEA, dextrose, or maltose) and further containing Cottonseed Hydrolysate in place of proteose peptone #3. A 0.15 M solution of asparagine was added at a continuous rate of 1000 μl/minute beginning at t=10 hours. At the end of the fermentation run, acrylonitrile-specific nitrile hydratase activity, amidase activity, asparaginase I activity, and biomass were measured. The results are summarized in Table 8.

TABLE 8

Enzymatic Activities and Biomass of *Rhodococcus rhodochrous* DAP 96253 Cells Following Continuous Induction with Asparagine

| Nitrile Hydratase Activity (Units/mg cdw) | Amidase Activity (Units/mg cdw) | Asparaginase I Activity (Units/mg cdw) | Biomass (g/l cww) |
|---|---|---|---|
| 159 | 22 | 16 | 16 |

G. *Rhodococcus rhodochrous* DAP 96253 cells grown on biphasic medium were used as the source of inoculum for a 20-liter fermentation run. A modified R3A medium was used that contained maltose (in place of dextrose) and Hy-Cotton 7803® as a substitute for proteose peptone #3. A 0.15 M solution of asparagine was added at a continuous rate of 476 μl/minute beginning at t=8 hours. At the end of the fermentation run, acrylonitrile-specific nitrile hydratase activity, amidase activity, and biomass were measured, and the results are summarized in Table 9.

TABLE 9

Enzymatic Activities and Biomass of *Rhodococcus rhodochrous* DAP 96253 Cells Following Continuous Induction with Asparagine

| Nitrile Hydratase Activity (Units/mg cdw) | Amidase Activity (Units/mg cdw) | Biomass (g/l cww) |
|---|---|---|
| 137 | 6 | 35 |

Example 4

Immobilization of *Rhodococcus* spp. Cells in DEAE-Cellulose Cross-Linked with Glutaraldehyde A modified process derived from the methods described in U.S. Pat. No. 4,229,536 and in Lopez-Gallego et al. (2005) *J. Biotechnol.* 119:70-75 is used to immobilize *Rhodococcus* spp. cells in a matrix comprising glutaraldehyde cross-linked DEAE-cellulose.

Preparation of Cells

*Rhodococcus* cells are grown in an appropriate culture medium (e.g., YEMEA-maltose+inducers, biphasic cultures, etc.) and harvested by centrifugation at 8,000 rpm for 10 minutes. The resulting cell pellet is resuspended in 100 ml of 50 mM phosphate buffer (pH 7.2) and centrifuged at 8,000 rpm for 10 minutes. This process of resuspending the cell pellet and centrifuging at 8,000 rpm for 10 minutes is repeated twice. The packed wet weight (ww) of the final cell sample is noted. The nitrile hydratase activity of a small sample of the cells is performed to assess the enzymatic activity of the whole cells.

Immobilization of Cells

An amount of DEAE-cellulose equivalent to that of the harvested *Rhodococcus* spp. cells is obtained, and the cells and the DEAE-cellulose are resuspended in 100 ml of deionized $H_2O$. A volume of a 25% solution of glutaraldehyde sufficient to achieve a final concentration of 0.5% is added with stirring to the mixture of cells/DEAE-cellulose. The mixture is stirred for 1 hour, after which 400 ml of deionized $H_2O$ is added with further mixing. While stirring, 50% (by weight solution) of polyethylenimine (PEI; MW 750,000) is added. Stirring proceeds until flocculation is completed. The flocculated mixture is filtered and extruded through a syringe of appropriate size. The immobilized cells are broken up into small pieces, dried overnight, and cut into granules of approximately 2-3 mm prior to use.

Example 5

Immobilization of *Rhodococcus* spp. Cells in Calcium Alginate and Hardening of Calcium Alginate Beads A process adapted from the method described in Bucke (1987) "Cell Immobilization in Calcium Alginate" in *Methods in Enzymology*, Vol. 135(B) (Academic Press, Inc., San Diego, Calif.; Mosbach, ed.) is used to immobilize *Rhodococcus* spp. cells in calcium alginate.

Preparation of Cells

The *Rhodococcus* spp. cells are prepared as described above in Example 4.

Immobilization of Cells 25 g of a 4% sodium alginate solution is produced by dissolving 1 g of sodium alginate in 24 ml of 50 mM Tris-HCl (pH 7.2). 25 mg of sodium metaperiodate is added to the alginate solution and stirred at 25° C. for 1 hour or until the alginate is completely dissolved. The cells prepared as described above are resuspended to a final volume of 50 ml in 50 mM Tris-HCl (pH 7.2) and then added to the sodium alginate solution with stirring. The resulting beads are extruded through a 27-gauge needle into 500 ml of a 0.1 M $CaCl_2$ solution. The needle is generally placed approximately two inches above the solution to prevent air entry into the beads and to prevent sticking of the beads. The beads are cured for 1 hour in the $CaCl_2$ solution, and the beads are then rinsed with water and stored at 4° C. in a 0.1 M $CaCl_2$ solution prior to use.

Hardening of Calcium Alginate Beads Comprising *Rhodococcus* spp. Cells

The calcium alginate beads prepared as outlined above may be further strengthened by cross-linking with PEI. The beads are incubated in 2 L of 0.5% PEI in a 0.1 M $CaCl_2$ solution (20 g of 50% PEI in a 0.1 M $CaCl_2$ solution). The pH of the final solution is adjusted to 7.0 with HCl or NaOH, if necessary, and the beads are incubated for 24 hours. The beads are then rinsed with water and stored at 4° C. in a 0.1 M $CaCl_2$ solution prior to use.

Many modifications and other embodiments of the inventions set forth herein will come to mind to one skilled in the art to which these inventions pertain having the benefit of the teachings presented in the foregoing descriptions. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A method for delaying a plant development process associated with ethylene biosynthesis comprising exposing a plant or plant part to one or more bacteria, wherein the one or more bacteria produce one or more enzymes including one or more enzymes selected from the group consisting of nitrile hydratases, amidases, asparaginases, and mixtures thereof and the bacteria are selected from the group consisting of *Rhodococcus* spp., *Brevibacterium ketoglutamicum*, and mixtures thereof, and wherein the one or more bacteria are exposed to the plant or plant part in a quantity sufficient to delay the plant development process.

2. The method of claim 1, wherein the one or more bacteria include *Rhodococcus* spp.

3. The method of claim 2, wherein the *Rhodococcus* spp. includes *Rhodococcus rhodochrous* DAP 96253 strain, *Rhodococcus* sp. DAP 96622 strain, *Rhodococcus erythropolis*, or mixtures thereof.

4. The method of claim 1, wherein the one or more bacteria are induced to produce one or more enzymes by exposure to an inducing agent selected from the group consisting of asparagine, glutamine, cobalt, urea, and mixtures thereof.

5. The method of claim 4, wherein the one or more bacteria are induced by exposure to asparagine.

6. The method of claim 4, wherein the one or more bacteria are induced by exposure to asparagine, cobalt, and urea.

7. The method of claim 1, wherein the plant or plant part is indirectly exposed to the one or more bacteria.

8. The method of claim 1, wherein the plant or plant part is directly exposed to the one or more bacteria.

9. The method of claim 1, wherein the plant development process is fruit or vegetable ripening.

10. The method of claim 9, wherein the plant part is a fruit or a vegetable.

11. The method of claim 10, wherein the fruit is a climacteric fruit.

12. The method of claim 11, wherein the climacteric fruit is selected from the group consisting of bananas, peaches, plums, nectarines, apples, tomatoes, pears and avocados.

13. The method of claim 10, wherein the fruit is a nonclimacteric fruit.

14. The method of claim 9, wherein the plant part is a cucumber.

15. The method of claim 1, wherein the plant part is a flower and the plant development process is flower senescence, wilting, abscission or petal closure.

16. The method of claim 15, wherein the flower is a carnation, rose, orchid, portulaca, malva, or begonia.

17. The method of claim 1, wherein the plant development process is leaf abscission.

18. An apparatus for delaying a plant development process associated with ethylene biosynthesis comprising a catalyst that comprises one or more bacteria that produce one or more enzymes including one or more enzymes selected from the group consisting of nitrile hydratases, amidases, asparaginases, and mixtures thereof and the bacteria are selected from the group consisting of *Rhodococcus* spp., *Brevibacterium ketoglutamicum*, and mixtures thereof, wherein the one or more bacteria are provided in a quantity sufficient to delay the plant development process.

19. The apparatus of claim 18, wherein the one or more bacteria include *Rhodococcus* spp.

20. The apparatus of claim 19, wherein the *Rhodococcus* spp. includes *Rhodococcus rhodochrous* DAP 96253 strain, *Rhodococcus* sp. DAP 96622 strain, *Rhodococcus erythropolis*, or mixtures thereof.

21. The apparatus of claim 18, wherein the one or more bacteria are induced to produce one or more enzymes by exposure to an inducing agent selected from the group consisting of asparagine, glutamine, cobalt, urea, and mixtures thereof.

22. The apparatus of claim 18, wherein the plant development process is selected from the group consisting of fruit or vegetable ripening, flower senescence, wilting, petal closure, and leaf abscission.

23. The apparatus of claim 18, wherein the one or more bacteria are immobilized in a matrix comprising cross-linked DEAE-cellulose, a matrix comprising alginate, a matrix comprising carrageen, a matrix comprising cross-linked alginate, a matrix comprising cross-linked carrageen, a matrix comprising polyacrylamide, or calcium alginate beads.

24. The apparatus of claim 23, wherein the matrix comprises cross-linked DEAE-cellulose, wherein the DEAE-cellulose is cross-linked with glutaraldehyde.

25. The apparatus of claim 18, wherein the catalyst is present in a catalyst module that is placed in, placed on, or affixed to a physical structure.

26. The apparatus of claim 18, further comprising a control device to adjust exposure of the catalyst to a plant or plant part.

27. The apparatus of claim 18, further comprising a monitoring device for monitoring the efficacy of the catalyst in delaying the plant development process.

28. The apparatus of claim 25, wherein the physical structure is selected from the group consisting of a film, sheet, coating layer, a slotted chamber, a box, a pouch, and a bag.

29. The apparatus of claim 25, wherein the catalyst module can be removed and replaced with a second catalyst module.

30. The apparatus of claim 25, wherein more than one catalyst module is placed in, placed on, or affixed to the physical structure.

31. The apparatus of claim 25, wherein the physical structure permits air flow into the catalyst module.

32. The apparatus of claim 31, further comprising an element for controlling the air flow into the catalyst module.

33. The apparatus of claim 25, wherein the physical structure is provided as a refrigerated structure.

34. The apparatus of claim 25, further comprising an element for controlling the moisture level in the physical structure.

35. The apparatus of claim 25, further comprising an element for regulating the carbon dioxide level in the physical structure.

36. An air-permeable catalyst apparatus for delaying a plant development process associated with ethylene biosynthesis comprising:
    a first layer; and
    a second layer that includes a catalyst comprising one or more bacteria that produce one or more enzymes including one or more enzymes selected from the group consisting of nitrile hydratases, amidases, and asparaginases, and mixtures thereof and the bacteria are selected from the group consisting of *Rhodococcus* spp., *Brevibacterium ketoglutamicum*, and mixtures thereof, wherein the one or more bacteria are provided in a quantity sufficient to delay the plant development process;
    wherein first layer provides structural integrity to the apparatus.

37. The apparatus of claim 36, wherein the one or more bacteria include *Rhodococcus* spp.

38. The apparatus of claim 37, wherein the *Rhodococcus* spp. includes *Rhodococcus rhodochrous* DAP 96253 strain, *Rhodococcus* sp. DAP 96622 strain, *Rhodococcus erythropolis*, or mixtures thereof.

39. The apparatus of claim 36, wherein the one or more bacteria are induced to produce one or more enzymes by exposure to an inducing agent selected from the group consisting of asparagine, glutamine, cobalt, urea, and mixtures thereof.

40. The apparatus of claim 36, wherein the plant development process is selected from the group consisting of fruit or vegetable ripening, flower senescence, and leaf abscission.

41. The catalyst apparatus of claim 36, further comprising a third layer such that the second layer is located between the first and third layers, wherein said third layer can be removed from said second layer to expose an adhesive layer that can be used to affix the catalyst apparatus to a separate structure.

42. The catalyst apparatus of claim 41, wherein said second layer is said adhesive layer.

43. The catalyst apparatus of claim 41, further comprising a fourth layer adjacent said third layer that can be removed from said third layer to expose an adhesive layer that can be used to affix the catalyst structure to a separate structure.

44. The catalyst apparatus of claim 43, wherein said third layer is said adhesive layer.

45. An air-permeable bag or pouch including the catalyst apparatus of claim 36.

46. A method for delaying a plant development process associated with ethylene biosynthesis comprising exposing a plant or plant part to an enzymatic extract of one or more bacteria that produce one or more enzymes including one or more enzymes selected from the group consisting of nitrile hydratases, amidases, asparaginases, and mixtures thereof and the bacteria are selected from the group consisting of *Rhodococcus* spp., *Brevibacterium ketoglutamicum*, and mixtures thereof, said bacteria being induced to produce said one or more enzymes by an inducing agent selected from the group consisting of asparagine, glutamine, cobalt, urea, and mixtures thereof and said enzymatic extract being exposed to the plant or plant part in a quantity sufficient to delay the plant development process.

47. A method for delaying a plant development process associated with ethylene biosynthesis comprising exposing a plant or plant part to one or more enzymes to delay the plant development process, wherein the one or more enzymes comprise nitrile hydratase, and wherein the plant or plant part is exposed to the one or more enzymes in a quantity sufficient to delay the plant development process.

48. The method of claim 47, wherein the step of exposing the plant or plant part to one or more enzymes includes exposing the plant or plant part to one or more bacteria producing the one or more enzymes.

49. The method of claim 1, wherein the plant part is a cut flower.

50. The method of claim 1, wherein delaying the plant development process results in increased shelf-life or facilitates longer-distance transportation of the plant or plant part.

51. The method of claim 1, wherein the one or more bacteria are immobilized and are placed in, placed on, or affixed to a physical structure suitable for transport or storage of the plant or plant part.

* * * * *

SEQUENCE LISTING

```
<160> NUMBER OF SEQ ID NOS: 13

<210> SEQ ID NO 1
<211> LENGTH: 229
<212> TYPE: PRT
<213> ORGANISM: Rhodococcus sp.

<400> SEQUENCE: 1

Met Asp Gly Ile His Asp Thr Gly Gly Met Thr Gly Tyr Gly Pro Val
 1               5                  10                  15

Pro Tyr Gln Lys Asp Glu Pro Phe Phe His Tyr Glu Trp Glu Gly Arg
                20                  25                  30

Thr Leu Ser Ile Leu Thr Trp Met His Leu Lys Gly Met Ser Trp Trp
            35                  40                  45

Asp Lys Ser Arg Phe Phe Arg Glu Ser Met Gly Asn Glu Asn Tyr Val
        50                  55                  60

Asn Glu Ile Arg Asn Ser Tyr Tyr Thr His Trp Leu Ser Ala Ala Glu
 65                  70                  75                  80

Arg Ile Leu Val Ala Asp Lys Ile Ile Thr Glu Glu Glu Arg Lys His
                85                  90                  95

Arg Val Gln Glu Ile Leu Glu Gly Arg Tyr Thr Asp Arg Asn Pro Ser
                100                 105                 110

Arg Lys Phe Asp Pro Ala Glu Ile Glu Lys Ala Ile Glu Arg Leu His
            115                 120                 125

Glu Pro His Ser Leu Ala Leu Pro Gly Ala Glu Pro Ser Phe Ser Leu
        130                 135                 140

Gly Asp Lys Val Lys Val Lys Asn Met Asn Pro Leu Gly His Thr Arg
145                 150                 155                 160

Cys Pro Lys Tyr Val Arg Asn Lys Ile Gly Glu Ile Val Thr Ser His
                165                 170                 175

Gly Cys Gln Ile Tyr Pro Glu Ser Ser Ser Ala Gly Leu Gly Asp Asp
            180                 185                 190

Pro Arg Pro Leu Tyr Thr Val Ala Phe Ser Ala Gln Glu Leu Trp Gly
        195                 200                 205

Asp Asp Gly Asn Gly Lys Asp Val Val Cys Val Asp Leu Trp Glu Pro
    210                 215                 220

Tyr Leu Ile Ser Ala
225

<210> SEQ ID NO 2
```

<211> LENGTH: 229
<212> TYPE: PRT
<213> ORGANISM: Nocardia sp.

<400> SEQUENCE: 2

```
Met Asp Gly Ile His Asp Thr Gly Gly Met Thr Gly Tyr Gly Pro Val
 1               5                  10                  15

Pro Tyr Gln Lys Asp Glu Pro Phe Phe His Tyr Glu Trp Glu Gly Arg
            20                  25                  30

Thr Leu Ser Ile Leu Thr Trp Met His Leu Lys Gly Met Ser Trp Trp
        35                  40                  45

Asp Lys Ser Arg Phe Phe Arg Glu Ser Met Gly Asn Glu Asn Tyr Val
50                  55                  60

Asn Glu Ile Arg Asn Ser Tyr Tyr Thr His Trp Leu Ser Ala Ala Glu
65                  70                  75                  80

Arg Ile Leu Val Ala Asp Lys Ile Ile Thr Glu Glu Arg Lys His
                85                  90                  95

Arg Val Gln Glu Ile Leu Glu Gly Arg Tyr Thr Asp Arg Asn Pro Ser
            100                 105                 110

Arg Lys Phe Asp Pro Ala Glu Ile Glu Lys Ala Ile Glu Arg Leu His
            115                 120                 125

Glu Pro His Ser Leu Ala Leu Pro Gly Ala Glu Pro Ser Phe Ser Leu
        130                 135                 140

Gly Asp Lys Val Lys Val Lys Asn Met Asn Pro Leu Gly His Thr Arg
145                 150                 155                 160

Cys Pro Lys Tyr Val Arg Asn Lys Ile Gly Glu Ile Val Thr Ser His
                165                 170                 175

Gly Cys Gln Ile Tyr Pro Glu Ser Ser Ser Ala Gly Leu Gly Asp Asp
            180                 185                 190

Pro Arg Pro Leu Tyr Thr Val Ala Phe Ser Ala Gln Glu Leu Trp Gly
            195                 200                 205

Asp Asp Gly Asn Gly Lys Asp Val Val Cys Val Asp Leu Trp Glu Pro
210                 215                 220

Tyr Leu Ile Ser Ala
225
```

<210> SEQ ID NO 3
<211> LENGTH: 229
<212> TYPE: PRT
<213> ORGANISM: Rhodococcus rhodochrous
<220> FEATURE:
<223> OTHER INFORMATION: Uncultured bacterium BD2

<400> SEQUENCE: 3

```
Met Asp Gly Ile His Asp Thr Gly Gly Met Thr Gly Tyr Gly Pro Val
 1               5                  10                  15

Pro Tyr Gln Lys Asp Glu Pro Phe Phe His Tyr Glu Trp Glu Gly Arg
            20                  25                  30

Thr Leu Ser Ile Leu Thr Trp Met His Leu Lys Gly Ile Ser Trp Trp
        35                  40                  45

Asp Lys Ser Arg Phe Phe Arg Glu Ser Met Gly Asn Glu Asn Tyr Val
50                  55                  60

Asn Glu Ile Arg Asn Ser Tyr Tyr Thr His Trp Leu Ser Ala Ala Glu
65                  70                  75                  80

Arg Ile Leu Val Ala Asp Lys Ile Ile Thr Glu Glu Arg Lys His
                85                  90                  95

Arg Val Gln Glu Ile Leu Glu Gly Arg Tyr Thr Asp Arg Lys Pro Ser
```

```
                100                 105                 110
Arg Lys Phe Asp Pro Ala Gln Ile Glu Lys Ala Ile Glu Arg Leu His
        115                 120                 125

Glu Pro His Ser Leu Ala Leu Pro Gly Ala Glu Pro Ser Phe Ser Leu
130                 135                 140

Gly Asp Lys Ile Lys Val Lys Ser Met Asn Pro Leu Gly His Thr Arg
145                 150                 155                 160

Cys Pro Lys Tyr Val Arg Asn Lys Ile Gly Ile Val Ala Tyr His
                165                 170                 175

Gly Cys Gln Ile Tyr Pro Glu Ser Ser Ser Ala Gly Leu Gly Asp Asp
        180                 185                 190

Pro Arg Pro Leu Tyr Thr Val Ala Phe Ser Ala Gln Glu Leu Trp Gly
        195                 200                 205

Asp Asp Gly Asn Gly Lys Asp Val Val Cys Val Asp Leu Trp Glu Pro
210                 215                 220

Tyr Leu Ile Ser Ala
225

<210> SEQ ID NO 4
<211> LENGTH: 166
<212> TYPE: PRT
<213> ORGANISM: Unknown
<220> FEATURE:
<223> OTHER INFORMATION: Uncultured bacterium BD2
<220> FEATURE:
<221> NAME/KEY: PEPTIDE
<222> LOCATION: (1)...(166)
<223> OTHER INFORMATION: Beta-subunit of nitrile hydratase

<400> SEQUENCE: 4

Met Asp Gly Ile His Asp Thr Gly Gly Met Thr Gly Tyr Gly Pro Val
1               5                   10                  15

Pro Tyr Gln Lys Asp Glu Pro Phe Phe His Tyr Glu Trp Glu Gly Arg
                20                  25                  30

Thr Leu Ser Ile Leu Thr Trp Met His Leu Lys Gly Ile Ser Trp Trp
            35                  40                  45

Asp Lys Ser Arg Phe Phe Arg Glu Ser Met Gly Asn Glu Asn Tyr Val
        50                  55                  60

Asp Glu Ile Arg Asn Ser Tyr Tyr Thr His Trp Leu Ser Ala Ala Glu
65                  70                  75                  80

Arg Ile Leu Val Ala Asp Lys Ile Ile Thr Glu Glu Arg Lys His
                85                  90                  95

Arg Val Gln Glu Ile Leu Glu Gly Arg Tyr Thr Asp Arg Lys Pro Ser
            100                 105                 110

Arg Lys Phe Asp Pro Ala Gln Ile Glu Lys Ala Ile Glu Arg Leu His
        115                 120                 125

Glu Pro His Ser Leu Ala Leu Pro Gly Ala Glu Pro Ser Phe Ser Leu
130                 135                 140

Gly Asp Lys Asn Gln Ser Glu Glu Tyr Glu Pro Ala Gly Thr His Thr
145                 150                 155                 160

Val Pro Glu Ile Cys Ala
                165

<210> SEQ ID NO 5
<211> LENGTH: 203
<212> TYPE: PRT
<213> ORGANISM: Rhodococcus sp.

<400> SEQUENCE: 5
```

```
Met Ser Glu His Val Asn Lys Tyr Thr Glu Tyr Glu Ala Arg Thr Lys
1               5                   10                  15

Ala Ile Glu Thr Leu Leu Tyr Glu Arg Gly Leu Ile Thr Pro Ala Ala
            20                  25                  30

Val Asp Arg Val Val Ser Tyr Tyr Glu Asn Glu Ile Gly Pro Met Gly
                35                  40                  45

Gly Ala Lys Val Val Ala Lys Ser Trp Val Asp Pro Glu Tyr Arg Lys
    50                  55                  60

Trp Leu Glu Glu Asp Ala Thr Ala Met Ala Ser Leu Gly Tyr Ala
65                  70                  75                  80

Gly Glu Gln Ala His Gln Ile Ser Ala Val Phe Asn Asp Ser Gln Thr
                85                  90                  95

His His Val Val Val Cys Thr Leu Cys Ser Cys Tyr Pro Trp Pro Val
                100                 105                 110

Leu Gly Leu Pro Pro Ala Trp Tyr Lys Ser Met Glu Tyr Arg Ser Arg
                115                 120                 125

Val Val Ala Asp Pro Arg Gly Val Leu Lys Arg Asp Phe Gly Phe Asp
            130                 135                 140

Ile Pro Asp Glu Val Glu Val Arg Val Trp Asp Ser Ser Ser Glu Ile
145                 150                 155                 160

Arg Tyr Ile Val Ile Pro Glu Arg Pro Ala Gly Thr Asp Gly Trp Ser
                165                 170                 175

Glu Asp Glu Leu Ala Lys Leu Val Ser Arg Asp Ser Met Ile Gly Val
                180                 185                 190

Ser Asn Ala Leu Thr Pro Gln Glu Val Ile Val
                195                 200

<210> SEQ ID NO 6
<211> LENGTH: 203
<212> TYPE: PRT
<213> ORGANISM: Rhodococcus rhodochrous

<400> SEQUENCE: 6

Met Ser Glu His Val Asn Lys Tyr Thr Glu Tyr Glu Ala Arg Thr Lys
1               5                   10                  15

Ala Ile Glu Thr Leu Leu Tyr Glu Arg Gly Leu Ile Thr Pro Ala Ala
            20                  25                  30

Val Asp Arg Val Val Ser Tyr Tyr Glu Asn Glu Ile Gly Pro Met Gly
                35                  40                  45

Gly Ala Lys Val Val Ala Lys Ser Trp Val Asp Pro Glu Tyr Arg Lys
    50                  55                  60

Trp Leu Glu Glu Asp Ala Thr Ala Met Ala Ser Leu Gly Tyr Ala
65                  70                  75                  80

Gly Glu Gln Ala His Gln Ile Ser Ala Val Phe Asn Asp Ser Gln Thr
                85                  90                  95

His His Val Val Val Cys Thr Leu Cys Ser Cys Tyr Pro Trp Pro Val
                100                 105                 110

Leu Gly Leu Pro Pro Ala Trp Tyr Lys Ser Met Glu Tyr Arg Ser Arg
                115                 120                 125

Val Val Ala Asp Pro Arg Gly Val Leu Lys Arg Asp Phe Gly Phe Asp
            130                 135                 140

Ile Pro Asp Glu Val Glu Val Arg Val Trp Asp Ser Ser Ser Glu Ile
145                 150                 155                 160

Arg Tyr Ile Val Ile Pro Glu Arg Pro Ala Gly Thr Asp Gly Trp Ser
                165                 170                 175
```

```
Glu Glu Glu Leu Thr Lys Leu Val Ser Arg Asp Ser Met Ile Gly Val
            180                 185                 190

Ser Asn Ala Leu Thr Pro Gln Glu Val Ile Val
            195                 200
```

<210> SEQ ID NO 7
<211> LENGTH: 180
<212> TYPE: PRT
<213> ORGANISM: Unknown
<220> FEATURE:
<223> OTHER INFORMATION: Uncultured bacterium SP1
<220> FEATURE:
<221> NAME/KEY: PEPTIDE
<222> LOCATION: (1)...(180)
<223> OTHER INFORMATION: Alpha-subunit of nitrile hydratase

<400> SEQUENCE: 7

```
Met Ser Glu His Val Asn Lys Tyr Thr Glu Tyr Glu Ala Arg Thr Lys
  1               5                  10                  15

Ala Val Glu Thr Leu Leu Tyr Glu Arg Gly Leu Ile Thr Pro Ala Ala
                 20                  25                  30

Val Asp Arg Val Val Ser Tyr Tyr Glu Asn Glu Ile Gly Pro Met Gly
             35                  40                  45

Gly Ala Lys Val Val Ala Lys Ser Trp Val Asp Pro Glu Tyr Arg Lys
         50                  55                  60

Trp Leu Glu Glu Asp Ala Thr Ala Ala Met Ala Ser Leu Gly Tyr Ala
 65                  70                  75                  80

Gly Glu Gln Ala His His Val Val Cys Thr Leu Cys Ser Cys Tyr
                     85                  90                  95

Pro Trp Pro Val Leu Gly Leu Pro Pro Ala Trp Tyr Lys Ser Met Glu
                100                 105                 110

Tyr Arg Ser Arg Val Val Ala Asp Pro Arg Gly Val Leu Lys Arg Asp
            115                 120                 125

Phe Gly Phe Asp Ile Pro Asp Glu Val Glu Val Arg Val Trp Asp Ser
        130                 135                 140

Ser Ser Glu Ile Arg Tyr Ile Val Ile Pro Glu Arg Pro Ala Gly Thr
145                 150                 155                 160

Asp Gly Trp Ser Glu Glu Glu Leu Thr Lys Leu Val Ser Arg Asp Ser
                165                 170                 175

Ile Ile Gly Val
            180
```

<210> SEQ ID NO 8
<211> LENGTH: 345
<212> TYPE: PRT
<213> ORGANISM: Rhodococcus rhodocrous

<400> SEQUENCE: 8

```
Met Arg His Gly Asp Ile Ser Ser Pro Thr Val Gly Val Ala
  1               5                  10                  15

Val Val Asn Tyr Lys Met Pro Arg Leu His Thr Lys Ala Asp Val Leu
                 20                  25                  30

Glu Asn Ala Arg Ala Ile Ala Lys Met Val Val Gly Met Lys Ala Gly
             35                  40                  45

Leu Pro Gly Met Asp Leu Val Val Phe Pro Glu Tyr Ser Thr Met Gly
         50                  55                  60

Ile Met Tyr Asp Asn Asp Glu Met Tyr Ala Thr Ala Thr Ile Pro
 65                  70                  75                  80
```

```
Gly Asp Glu Thr Asp Ile Phe Ala Gln Ala Cys Arg Asp Ala Lys Thr
                85                  90                  95

Trp Gly Val Phe Ser Ile Thr Gly Glu Arg His Glu Asp His Pro Asn
            100                 105                 110

Lys Pro Pro Tyr Asn Thr Leu Val Leu Ile Asn Asp Gln Gly Glu Ile
        115                 120                 125

Val Gln Lys Tyr Arg Lys Ile Leu Pro Trp Thr Pro Ile Glu Gly Trp
    130                 135                 140

Tyr Pro Gly Gly Gln Thr Tyr Val Thr Asp Gly Pro Lys Gly Leu Lys
145                 150                 155                 160

Ile Ser Leu Ile Ile Cys Asp Asp Gly Asn Tyr Pro Glu Ile Trp Arg
                165                 170                 175

Asp Cys Ala Met Lys Gly Ala Glu Leu Ile Val Arg Pro Gln Gly Tyr
            180                 185                 190

Met Tyr Pro Ser Lys Glu Gln Gln Val Leu Met Ala Lys Ala Met Ala
        195                 200                 205

Trp Ala Asn Asn Cys Tyr Val Ala Val Ala Asn Ala Thr Gly Phe Asp
    210                 215                 220

Gly Val Tyr Ser Tyr Phe Gly His Ser Ala Ile Ile Gly Phe Asp Gly
225                 230                 235                 240

Arg Thr Leu Gly Glu Cys Gly Glu Glu Asp Tyr Gly Val Gln Tyr Ala
                245                 250                 255

Gln Leu Ser Leu Ser Thr Ile Arg Asp Ala Arg Ala Asn Asp Gln Ser
            260                 265                 270

Gln Asn His Leu Phe Lys Leu Leu His Arg Gly Tyr Thr Gly Val Phe
        275                 280                 285

Ala Gly Gly Asp Gly Asp Lys Gly Val Ala Asp Cys Pro Phe Asp Phe
    290                 295                 300

Tyr Arg Asn Trp Val Asn Asp Ala Glu Ala Thr Gln Lys Ala Val Glu
305                 310                 315                 320

Ala Ile Thr Arg Glu Thr Ile Gly Val Ala Asp Cys Pro Val Tyr Asp
                325                 330                 335

Leu Pro Ser Glu Lys Thr Met Asp Ala
            340                 345

<210> SEQ ID NO 9
<211> LENGTH: 345
<212> TYPE: PRT
<213> ORGANISM: Nocardia farcinica

<400> SEQUENCE: 9

Met Arg His Gly Asp Ile Ser Ser Pro Asp Thr Val Gly Val Ala
  1               5                  10                  15

Val Val Asn Tyr Lys Met Pro Arg Leu His Thr Lys Ala Glu Val Leu
            20                  25                  30

Asp Asn Cys Arg Arg Ile Ala Asp Met Leu Val Gly Met Lys Ser Gly
        35                  40                  45

Leu Pro Gly Met Asp Leu Val Val Phe Pro Glu Tyr Ser Thr Gln Gly
    50                  55                  60

Ile Met Tyr Asp Glu Gln Glu Met Tyr Asp Thr Ala Ala Thr Val Pro
65                  70                  75                  80

Gly Glu Glu Thr Ala Ile Phe Ser Ala Ala Cys Arg Glu Ala Gly Val
                85                  90                  95

Trp Gly Val Phe Ser Ile Thr Gly Glu Gln His Glu Asp His Pro Arg
            100                 105                 110
```

```
Lys Pro Pro Tyr Asn Thr Leu Val Leu Ile Asp Asp His Gly Glu Ile
            115                 120                 125

Val Gln Lys Tyr Arg Lys Ile Leu Pro Trp Cys Pro Ile Glu Gly Trp
    130                 135                 140

Tyr Pro Gly Asp Thr Thr Tyr Val Thr Glu Gly Pro Lys Gly Leu Lys
145                 150                 155                 160

Ile Ser Leu Ile Val Cys Asp Asp Gly Asn Tyr Pro Glu Ile Trp Arg
                165                 170                 175

Asp Cys Ala Met Lys Gly Ala Glu Leu Ile Val Arg Cys Gln Gly Tyr
            180                 185                 190

Met Tyr Pro Ser Lys Asp Gln Gln Val Leu Met Ala Lys Ala Met Ala
    195                 200                 205

Trp Ala Asn Asn Cys Tyr Val Ala Val Ala Asn Ala Ala Gly Phe Asp
210                 215                 220

Gly Val Tyr Ser Tyr Phe Gly His Ser Ala Leu Ile Gly Phe Asp Gly
225                 230                 235                 240

Arg Thr Leu Gly Glu Thr Gly Glu Glu Tyr Gly Ile Gln Tyr Ala
                245                 250                 255

Gln Leu Ser Ile Ser Ala Ile Arg Asp Ala Arg Ala His Asp Gln Ser
                260                 265                 270

Gln Asn His Leu Phe Lys Leu Leu His Arg Gly Tyr Ser Gly Val His
            275                 280                 285

Ala Ala Gly Asp Gly Asp Arg Gly Val Ala Asp Cys Pro Phe Glu Phe
290                 295                 300

Tyr Lys Leu Trp Val Thr Asp Ala Gln Gln Ala Arg Glu Arg Val Glu
305                 310                 315                 320

Ala Ile Thr Arg Asp Thr Val Gly Val Ala Asp Cys Arg Val Gly Ser
                325                 330                 335

Leu Pro Val Glu Gln Thr Leu Glu Ala
            340                 345

<210> SEQ ID NO 10
<211> LENGTH: 346
<212> TYPE: PRT
<213> ORGANISM: Pseudomonas aeruginosa

<400> SEQUENCE: 10

Met Arg His Gly Asp Ile Ser Ser Ser Asn Asp Thr Val Gly Val Ala
1               5                   10                  15

Val Val Asn Tyr Lys Met Pro Arg Leu His Thr Ala Ala Glu Val Leu
            20                  25                  30

Asp Asn Ala Arg Lys Ile Ala Glu Met Ile Val Gly Met Lys Gln Gly
        35                  40                  45

Leu Pro Gly Met Asp Leu Val Val Phe Pro Glu Tyr Ser Leu Gln Gly
    50                  55                  60

Ile Met Tyr Asp Pro Ala Glu Met Met Glu Thr Ala Val Ala Ile Pro
65                  70                  75                  80

Gly Glu Glu Thr Glu Ile Phe Ser Arg Ala Cys Arg Lys Ala Asn Val
                85                  90                  95

Trp Gly Val Phe Ser Leu Thr Gly Glu Arg His Glu Glu His Pro Arg
            100                 105                 110

Lys Ala Pro Tyr Asn Thr Leu Val Leu Ile Asp Asn Asn Gly Glu Ile
            115                 120                 125

Val Gln Lys Tyr Arg Lys Ile Ile Pro Trp Cys Pro Ile Glu Gly Trp
    130                 135                 140
```

```
Tyr Pro Gly Gly Gln Thr Tyr Val Ser Glu Gly Pro Lys Gly Met Lys
145                 150                 155                 160

Ile Ser Leu Ile Ile Cys Asp Asp Gly Asn Tyr Pro Glu Ile Trp Arg
                165                 170                 175

Asp Cys Ala Met Lys Gly Ala Glu Leu Ile Val Arg Cys Gln Gly Tyr
            180                 185                 190

Met Tyr Pro Ala Lys Asp Gln Gln Val Met Met Ala Lys Ala Met Ala
        195                 200                 205

Trp Ala Asn Asn Cys Tyr Val Ala Val Ala Asn Ala Ala Gly Phe Asp
210                 215                 220

Gly Val Tyr Ser Tyr Phe Gly His Ser Ala Ile Ile Gly Phe Asp Gly
225                 230                 235                 240

Arg Thr Leu Gly Glu Cys Gly Glu Glu Met Gly Ile Gln Tyr Ala
                245                 250                 255

Gln Leu Ser Leu Ser Gln Ile Arg Asp Ala Arg Ala Asn Asp Gln Ser
                260                 265                 270

Gln Asn His Leu Phe Lys Ile Leu His Arg Gly Tyr Ser Gly Leu Gln
            275                 280                 285

Ala Ser Gly Asp Gly Asp Arg Gly Leu Ala Glu Cys Pro Phe Glu Phe
        290                 295                 300

Tyr Arg Thr Trp Val Thr Asp Ala Glu Lys Ala Arg Glu Asn Val Glu
305                 310                 315                 320

Arg Leu Thr Arg Ser Thr Thr Gly Val Ala Gln Cys Pro Val Gly Arg
                325                 330                 335

Leu Pro Tyr Glu Gly Leu Glu Lys Glu Ala
                340                 345

<210> SEQ ID NO 11
<211> LENGTH: 339
<212> TYPE: PRT
<213> ORGANISM: Heliobacter pylori

<400> SEQUENCE: 11

Met Arg His Gly Asp Ile Ser Ser Pro Asp Thr Val Gly Val Ala
1               5                   10                  15

Val Val Asn Tyr Lys Met Pro Arg Leu His Thr Lys Asn Glu Val Leu
                20                  25                  30

Glu Asn Cys Arg Asn Ile Ala Lys Val Ile Gly Gly Val Lys Gln Gly
            35                  40                  45

Leu Pro Gly Leu Asp Leu Ile Ile Phe Pro Glu Tyr Ser Thr His Gly
        50                  55                  60

Ile Met Tyr Asp Arg Gln Glu Met Phe Asp Thr Ala Ala Ser Val Pro
65                  70                  75                  80

Gly Glu Glu Thr Ala Ile Leu Ala Glu Ala Cys Lys Lys Asn Lys Val
                85                  90                  95

Trp Gly Val Phe Ser Leu Thr Gly Glu Lys His Glu Gln Ala Lys Lys
            100                 105                 110

Asn Pro Tyr Asn Thr Leu Ile Leu Val Asn Asp Lys Gly Glu Ile Val
        115                 120                 125

Gln Lys Tyr Arg Lys Ile Leu Pro Trp Cys Pro Ile Glu Cys Trp Tyr
130                 135                 140

Pro Gly Asp Lys Thr Tyr Val Val Asp Gly Pro Lys Gly Leu Lys Val
145                 150                 155                 160

Ser Leu Ile Ile Cys Asp Asp Gly Asn Tyr Pro Glu Ile Trp Arg Asp
                165                 170                 175
```

```
Cys Ala Met Arg Gly Ala Glu Leu Ile Val Arg Cys Gln Gly Tyr Met
            180                 185                 190

Tyr Pro Ala Lys Glu Gln Gln Ile Ala Ile Val Lys Ala Met Ala Trp
            195                 200                 205

Ala Asn Gln Cys Tyr Val Ala Val Ala Asn Ala Thr Gly Phe Asp Gly
            210                 215                 220

Val Tyr Ser Tyr Phe Gly His Ser Ser Ile Ile Gly Phe Asp Gly His
225                 230                 235                 240

Thr Leu Gly Glu Cys Gly Glu Glu Asn Gly Leu Gln Tyr Ala Gln
            245                 250                 255

Leu Ser Val Gln Gln Ile Arg Asp Ala Arg Lys Tyr Asp Gln Ser Gln
            260                 265                 270

Asn Gln Leu Phe Lys Leu Leu His Arg Gly Tyr Ser Gly Val Phe Ala
            275                 280                 285

Ser Gly Asp Gly Asp Lys Gly Val Ala Glu Cys Pro Phe Glu Phe Tyr
            290                 295                 300

Lys Thr Trp Val Asn Asp Pro Lys Lys Ala Gln Glu Asn Val Glu Lys
305                 310                 315                 320

Phe Thr Arg Pro Ser Val Gly Val Ala Ala Cys Pro Val Gly Asp Leu
            325                 330                 335

Pro Thr Lys

<210> SEQ ID NO 12
<211> LENGTH: 339
<212> TYPE: PRT
<213> ORGANISM: Heliobacter pylori

<400> SEQUENCE: 12

Met Arg His Gly Asp Ile Ser Ser Ser Pro Asp Thr Val Gly Val Ala
 1               5                  10                  15

Val Val Asn Tyr Lys Met Pro Arg Leu His Thr Lys Asn Glu Val Leu
            20                  25                  30

Glu Asn Cys Arg Asn Ile Ala Lys Val Ile Gly Gly Val Lys Gln Gly
        35                  40                  45

Leu Pro Gly Leu Asp Leu Ile Ile Phe Pro Glu Tyr Ser Thr His Gly
    50                  55                  60

Ile Met Tyr Asp Arg Gln Glu Met Phe Asp Thr Ala Ala Ser Val Pro
65                  70                  75                  80

Gly Glu Glu Thr Ala Ile Phe Ala Glu Ala Cys Lys Lys Asn Lys Val
            85                  90                  95

Trp Gly Val Phe Ser Leu Thr Gly Glu Lys His Glu Gln Ala Lys Lys
            100                 105                 110

Asn Pro Tyr Asn Thr Leu Ile Leu Val Asn Asp Lys Gly Glu Ile Val
            115                 120                 125

Gln Lys Tyr Arg Lys Ile Leu Pro Trp Cys Pro Ile Glu Cys Trp Tyr
        130                 135                 140

Pro Gly Asp Lys Thr Tyr Val Val Asp Gly Pro Lys Gly Leu Lys Val
145                 150                 155                 160

Ser Leu Ile Ile Cys Asp Asp Gly Asn Tyr Pro Glu Ile Trp Arg Asp
            165                 170                 175

Cys Ala Met Arg Gly Ala Glu Leu Ile Val Arg Cys Gln Gly Tyr Met
            180                 185                 190

Tyr Pro Ala Lys Glu Gln Gln Ile Ala Ile Val Lys Ala Met Ala Trp
            195                 200                 205

Ala Asn Gln Cys Tyr Val Ala Val Ala Asn Ala Thr Gly Phe Asp Gly
            210                 215                 220
```

```
                    210                 215                 220
Val Tyr Ser Tyr Phe Gly His Ser Ser Ile Ile Gly Phe Asp Gly His
225                 230                 235                 240

Thr Leu Gly Glu Cys Gly Glu Glu Asn Gly Leu Gln Tyr Ala Gln
                245                 250                 255

Leu Ser Val Gln Gln Ile Arg Asp Ala Arg Lys Tyr Asp Gln Ser Gln
                260                 265                 270

Asn Gln Leu Phe Lys Leu Leu His Arg Gly Tyr Ser Gly Val Phe Ala
                275                 280                 285

Ser Gly Asp Gly Asp Lys Gly Val Ala Glu Cys Pro Phe Glu Phe Tyr
        290                 295                 300

Lys Thr Trp Val Asn Asp Pro Lys Lys Ala Gln Glu Asn Val Glu Lys
305                 310                 315                 320

Ile Thr Arg Pro Ser Val Gly Val Ala Ala Cys Pro Val Gly Asp Leu
                325                 330                 335

Pro Thr Lys

<210> SEQ ID NO 13
<211> LENGTH: 346
<212> TYPE: PRT
<213> ORGANISM: Pseudomonas aeruginosa

<400> SEQUENCE: 13

Met Arg His Gly Asp Ile Ser Ser Asn Asp Thr Val Gly Val Ala
1               5                   10                  15

Val Val Asn Tyr Lys Met Pro Arg Leu His Thr Ala Ala Glu Val Leu
                20                  25                  30

Asp Asn Ala Arg Lys Ile Ala Asp Met Ile Val Gly Met Lys Gln Gly
                35                  40                  45

Leu Pro Gly Met Asp Leu Val Val Phe Pro Glu Tyr Ser Leu Gln Gly
        50                  55                  60

Ile Met Tyr Asp Pro Ala Glu Met Met Glu Thr Ala Val Ala Ile Pro
65                  70                  75                  80

Gly Glu Glu Thr Glu Ile Phe Ser Arg Ala Cys Arg Lys Ala Asn Val
                85                  90                  95

Trp Gly Val Phe Ser Leu Thr Gly Glu Arg His Glu Glu His Pro Arg
                100                 105                 110

Lys Ala Pro Tyr Asn Thr Leu Val Leu Ile Asp Asn Asn Gly Glu Ile
                115                 120                 125

Val Gln Lys Tyr Arg Lys Ile Ile Pro Trp Cys Pro Ile Glu Gly Trp
        130                 135                 140

Tyr Pro Gly Gly Gln Thr Tyr Val Ser Glu Gly Pro Lys Gly Met Lys
145                 150                 155                 160

Ile Ser Leu Ile Ile Cys Asp Asp Pro Asn Tyr Pro Glu Ile Trp Arg
                165                 170                 175

Asp Cys Ala Met Lys Gly Ala Glu Leu Ile Val Arg Cys Gln Gly Tyr
                180                 185                 190

Met Tyr Pro Ala Lys Asp Gln Gln Val Met Met Ala Lys Ala Met Ala
        195                 200                 205

Trp Ala Asn Asn Cys Tyr Val Ala Val Ala Asn Ala Ala Gly Phe Asp
210                 215                 220

Gly Val Tyr Ser Tyr Phe Gly His Ser Ala Ile Ile Gly Phe Asp Gly
225                 230                 235                 240

Arg Thr Leu Gly Glu Cys Gly Glu Glu Glu Met Gly Ile Gln Tyr Ala
                245                 250                 255
```

-continued

```
Gln Leu Ser Leu Ser Gln Ile Arg Asp Ala Arg Ala Asn Asp Gln Ser
            260                 265                 270

Gln Asn His Leu Phe Lys Ile Leu His Arg Gly Tyr Ser Gly Leu Gln
        275                 280                 285

Ala Ser Gly Asp Gly Asp Arg Gly Leu Ala Glu Cys Pro Phe Glu Phe
        290                 295                 300

Tyr Arg Thr Trp Val Thr Asp Ala Glu Lys Ala Arg Asp Asn Val Glu
305                 310                 315                 320

Arg Leu Thr Arg Ser Thr Thr Gly Val Ala Gln Cys Pro Val Gly Arg
                325                 330                 335

Leu Pro Tyr Glu Gly Leu Glu Lys Glu Ala
                340                 345
```